US011352400B2

(12) United States Patent
Hirsch et al.

(10) Patent No.: US 11,352,400 B2
(45) Date of Patent: *Jun. 7, 2022

(54) PI3K GAMMA INHIBITOR PEPTIDE FOR TREATMENT OF RESPIRATORY SYSTEM DISEASES

(71) Applicant: Kither Biotech S.r.I., Turin (IT)

(72) Inventors: Emilio Hirsch, Turin (IT); Alessandra Ghigo, Savigliano (IT)

(73) Assignee: KITHER BIOTECH SRL, Turin (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/911,485

(22) Filed: Jun. 25, 2020

(65) Prior Publication Data

US 2020/0317740 A1 Oct. 8, 2020

Related U.S. Application Data

(60) Division of application No. 16/538,987, filed on Aug. 13, 2019, now Pat. No. 10,730,921, which is a continuation of application No. 15/539,339, filed as application No. PCT/IB2015/059880 on Dec. 22, 2015, now Pat. No. 10,421,794.

(30) Foreign Application Priority Data

Dec. 24, 2014 (IT) .......................... TO2014A001105

(51) Int. Cl.
| | |
|---|---|
| *C07K 14/47* | (2006.01) |
| *A61P 11/00* | (2006.01) |
| *A61K 38/00* | (2006.01) |
| *A61K 45/06* | (2006.01) |

(52) U.S. Cl.
CPC ........ *C07K 14/4703* (2013.01); *A61K 38/005* (2013.01); *A61K 45/06* (2013.01); *A61P 11/00* (2018.01); *A61K 38/00* (2013.01); *C07K 2319/10* (2013.01)

(58) Field of Classification Search
None
See application file for complete search history.

(56) References Cited

U.S. PATENT DOCUMENTS

| | | | | |
|---|---|---|---|---|
| 10,421,794 | B2* | 9/2019 | Hirsch | A61K 45/06 |
| 10,730,921 | B2* | 8/2020 | Hirsch | C07K 14/4703 |
| 2006/0189605 | A1 | 8/2006 | Konetzki et al. | |
| 2010/0190698 | A1* | 7/2010 | Watt | C07K 14/4703 514/1.1 |
| 2011/0166149 | A1 | 7/2011 | Dellamary et al. | |
| 2018/0086798 | A1 | 3/2018 | Hirsch et al. | |
| 2019/0367571 | A1 | 12/2019 | Hirsch et al. | |

FOREIGN PATENT DOCUMENTS

| | | |
|---|---|---|
| WO | WO 2004/026285 A2 | 4/2004 |
| WO | WO 2006/089106 A2 | 8/2006 |
| WO | WO 2009/100305 A1 | 8/2009 |
| WO | WO 2011/031896 A2 | 3/2011 |

OTHER PUBLICATIONS

Perino et al. "Integrating Cardiac PIP3 and cAMP Signaling through a PKA Anchoring Function of p110gamma" Molecular Cell 42: 84-95. (Year: 2011).*
Bechara et al. "Cell-penetrating peptides: 20 years later, where do we stand?" FEBS Letters 587:1693-1702. (Year: 2013).*
Marwick et al. "Phosphatidylinsoitol 3-kinase isoforms as targets in respiratory disease" Therapeutic Advances in Respiratory Disease 4:19-34. (Year: 2010).*
Barnes, P. J., "New Drugs for Asthma," Nat Rev Drug Discov 3:831-844 (2004).
Bechara C and Sagan "Cell-penetrating peptides: 20 years later, where do we stand?" FEBS Letters 587: 1693-1702 (2013).
Cain et al., "Different PI 3-kinase inhibitors have distinct effects on endothelial permeability and leukocyte transmigration", International Journal Of Biochemistry And Cell Biology, vol. 44, No. 11, Jul. 17, 2012, pp. 1929-1936.
Derossi et al., "Trojan peptides: the penetratin system for intracellular delivery", Trends In Cell Biology, vol. 8, No. 2, Feb. 1, 1998, pp. 84-87.
Doukas et al., "Aerosolized Phosphoinositide 3-Kinase / Inhibitor TG100-115 [3-[2,4-Diamino-6-(3-hydroxyphenyl)pteridin-7-yl]phenol] as a Therapeutic Candidate for Asthma and Chronic Obstructive Pulmonary Disease", Journal of Pharmacology and Experimental Therapeutics,, vol. 328, No. 3, Dec. 4, 2008, pp. 758-765.
Duan, W., et al., "An anti-inflammatory role for a phosphoinositide 3-kinase inhibitor LY294002 in a mouse asthma model," Int Immunopharmacol 5:495-502 (2005).
Fanelli et al., "Pulmonary-derived phosphoinositide 3-kinase gamma (PI3KÎ) contributes to ventilator-induced lung injury and edema", Intensive Care Medicine, vol. 36, No. 11, Aug. 19, 2010, pp. 1935-1945.
Ghigo et al., "Isoform selective phosphoinositide 3-kinase gamma and delta inhibitors and their therapeutic potential", Recent patents on inflammation & allergy drug discovery, vol. 2, No. 1, Jan. 2008, pp. 1-10.
Ghigo et al., "PI3K inhibition in inflammation: Toward tailored therapies for specific diseases", Bioessays, vol. 32, No. 3, Mar. 2010, pp. 185-196.
Hirsch et al., "Taming the PI3K team to hold inflammation and cancer at bay", Pharmacology And Therapeutics, vol. 118, No. 2, May 1, 2008, pp. 192-205.
Hirsch, E., et al., "Twice upon a time: PI3K's secret double life exposed," Trends Biochem Sci 34(5):244-248 (2009).

(Continued)

*Primary Examiner* — Sudhakar Katakam
*Assistant Examiner* — Zachary J Miknis
(74) *Attorney, Agent, or Firm* — Nixon & Vanderhye, PC

(57) ABSTRACT

Fusion peptide comprising: i) an amino acid sequence as defined in SEQ ID No.: 1 or a related homolog having at least 90% identity with SEQ ID No.: 1 and having the ability of the sequence SEQ ID No.: 1 to inhibit the kinase-independent function of PI3Kγ, and ii) a peptide having the ability to penetrate a cell.

11 Claims, 11 Drawing Sheets

Specification includes a Sequence Listing.

(56) References Cited

OTHER PUBLICATIONS

International Search Report and Written Opinion of the ISA for PCT/IB2015/059880, dated Apr. 7, 2016, 15 pages.

Ito et al., "Therapeutic potential of phosphatidylinositol 3-kinase inhibitors in inflammatory respiratory disease", Journal of Pharmacology and Experimental Therapeutics, vol. 321, No. 1, Jan. 1, 2007, pp. 1-8.

Laffargue, M., et al., "Phosphoinositide 3-Kinase γ Is an Essential Amplifier of Mast Cell Function," Immunity 16:441-451 (2002).

Marwick et al., "Phosphatidylinositol 3-kinase isoforms as targets in respiratory disease", Therapeutic advances in respiratory disease, vol. 4, No. 1, Feb. 1, 2010, pp. 19-34.

Moschos et al., "Lung delivery studies using siRNA conjugated to TAT(48-60) and penetratin reveal peptide induced reduction in gene expression and induction of innate immunity", Bioconjugate Chemistry, vol. 18, No. 5, Sep. 1, 2007, pp. 1450-1459.

Myou et al., "Blockade of Inflammation and Airway Hyperresponsiveness in Immune-sensitized Mice by Dominant-Negative Phosphoinositide 3-Kinase-TAT", Journal of Experimental Medicine, vol. 198, No. 10, Nov. 10, 2003, pp. 1573-1582.

Perino, et al., "Integrating Cardiac PIP3 and cAMP Signaling through PKA Anchoring Function of p110gamma" Molecular Cell 42: 84-95. (2011).

Thomas, M. J., et al., "Airway inflammation: chemokine-induced neutrophilia and the class I phosphoinositide 3-kinases," Eur J Immunol 35:1283-1291 (2005).

Matthews et al., Molecular Biomedicine 1:11 (2020).

Depreter et al., International Journal of Pharmaceutics 447:251-280 (2013).

Respaud et al., Expert Opinion on Drug Delivery 12(5): 1-13 (2014).

Hertel et al., Advanced Drug Delivery Reviews 93:79-94 (2015).

Labiris et al., Journal of Clinical Pharmacology 56:588-599 (2003).

\* cited by examiner

Figure 1
A
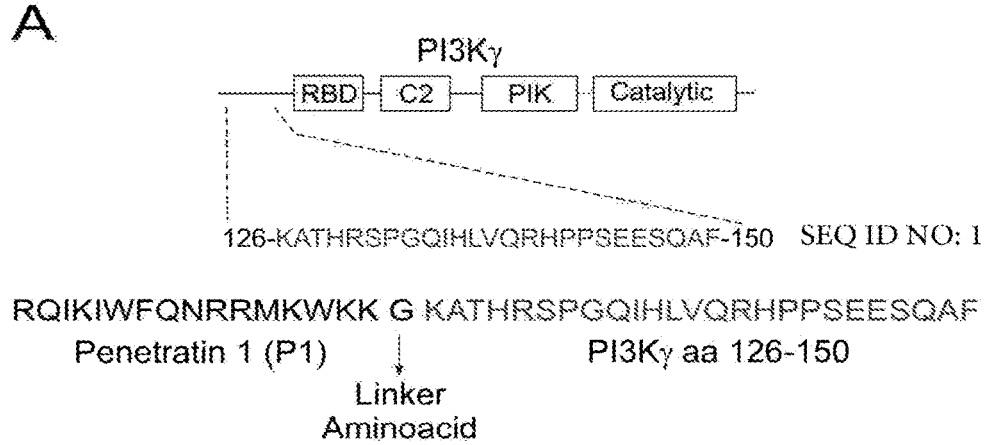
B
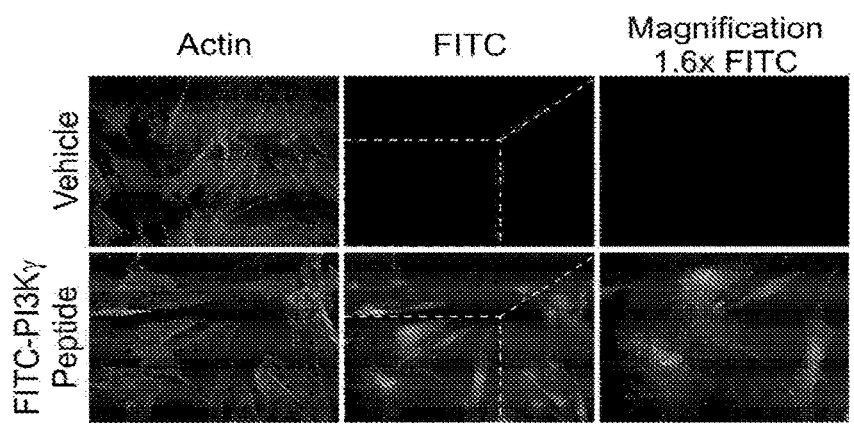

Figure 1_cont
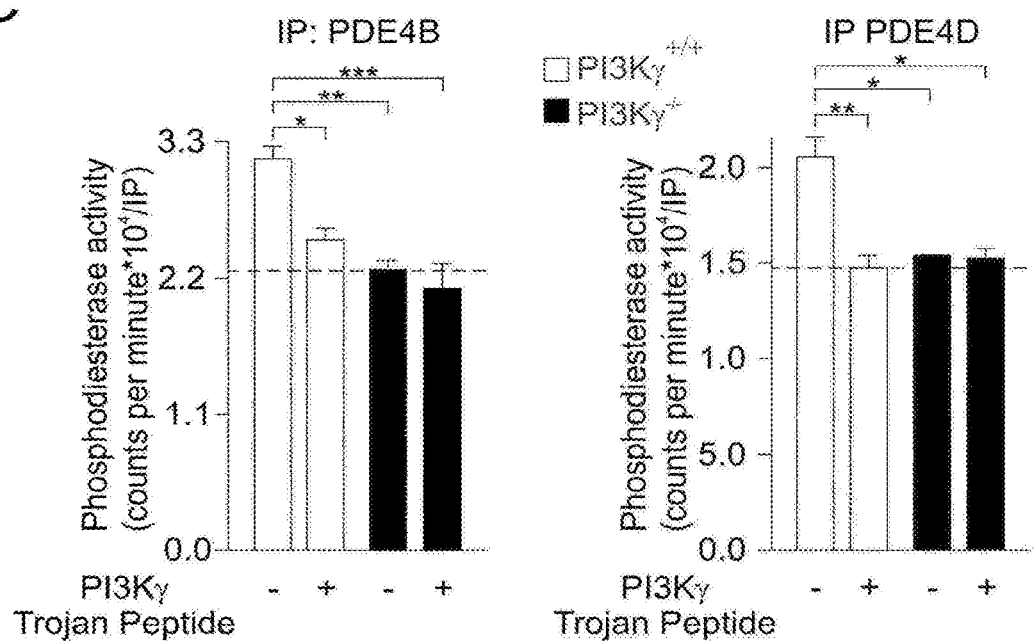
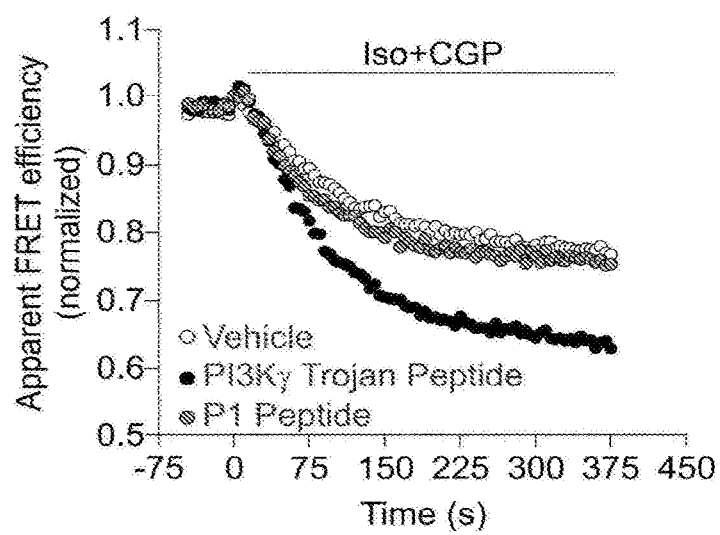
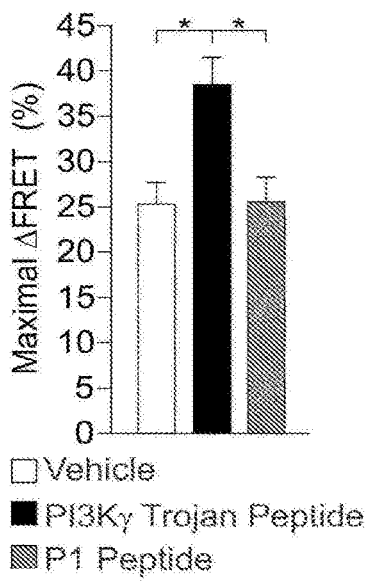

Figure 2
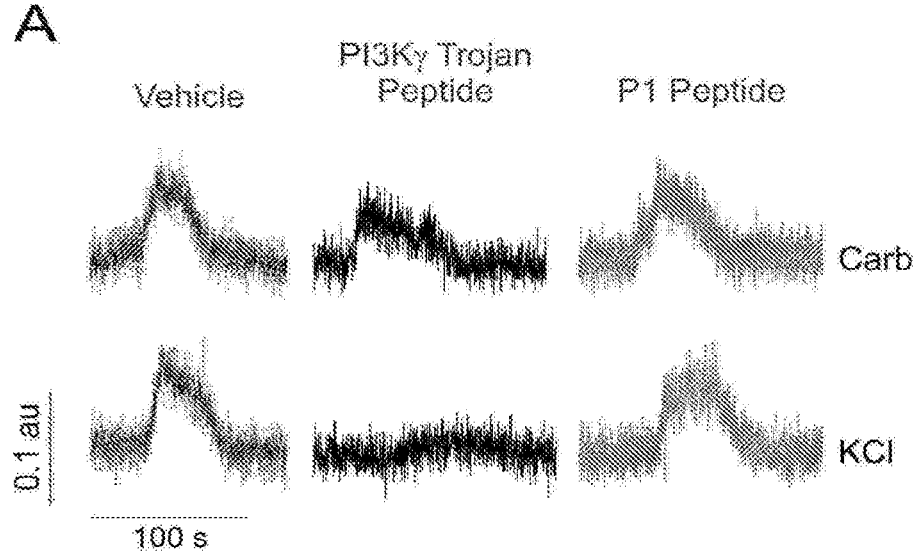
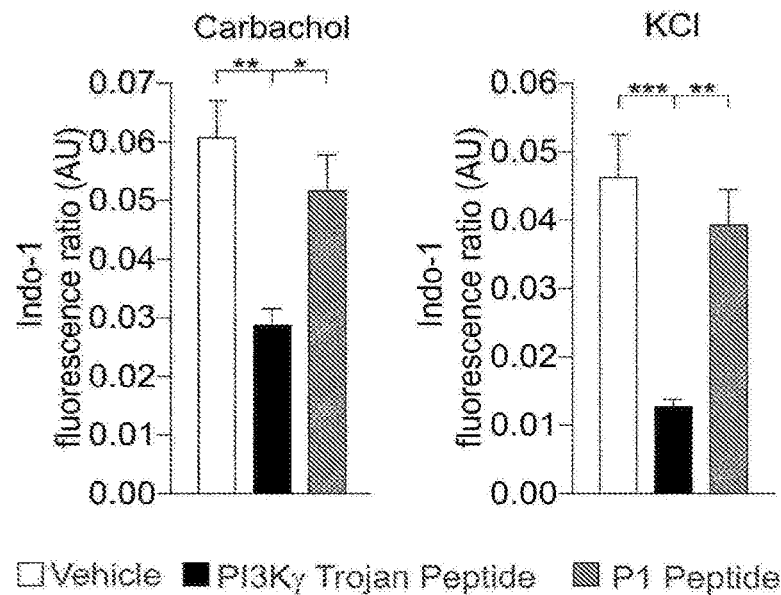

Figure 2_cont
C
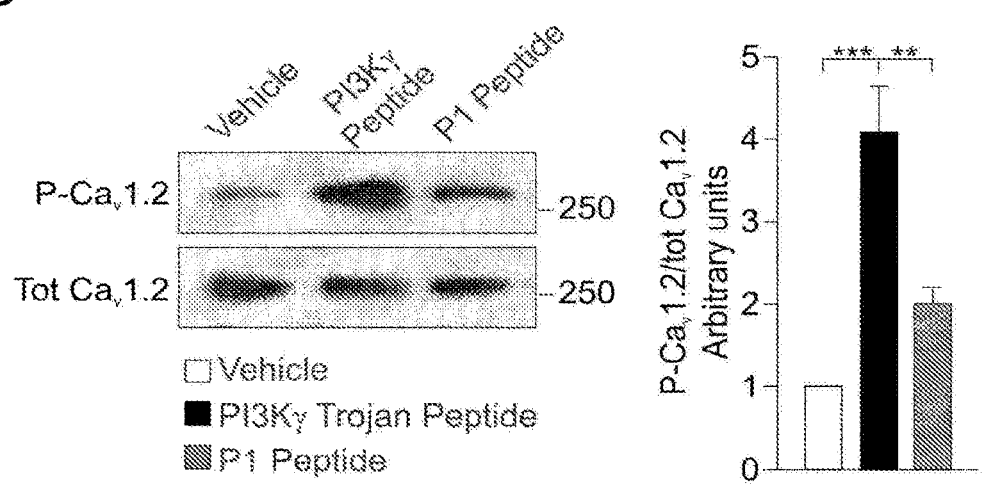

Figure 3
A
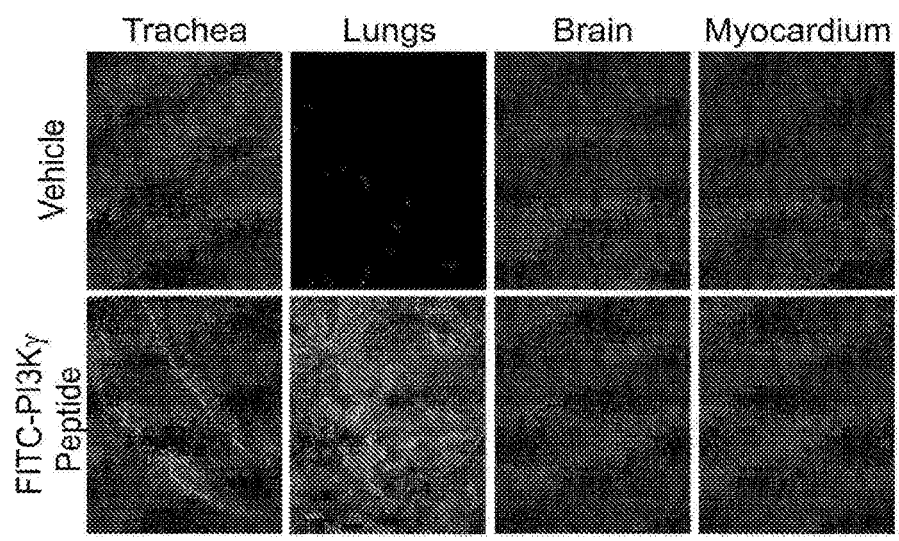
B
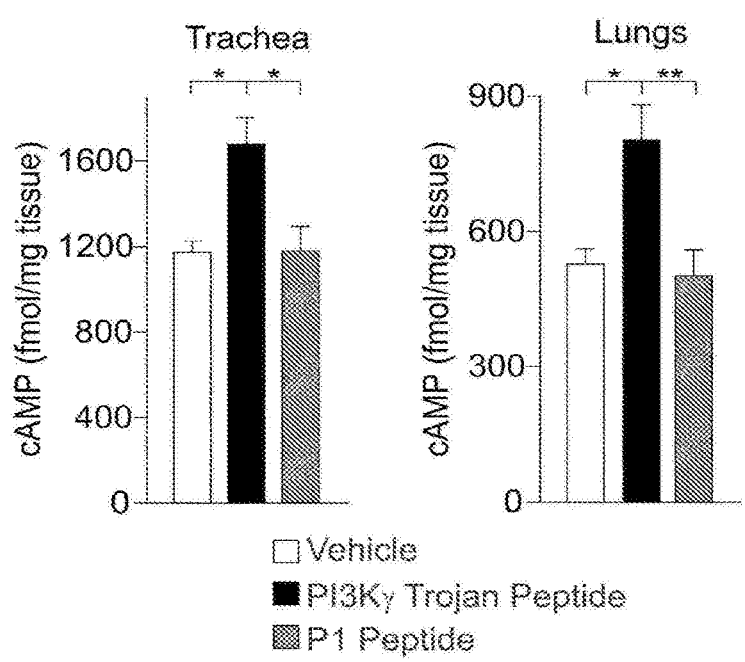

Figure 3_cont
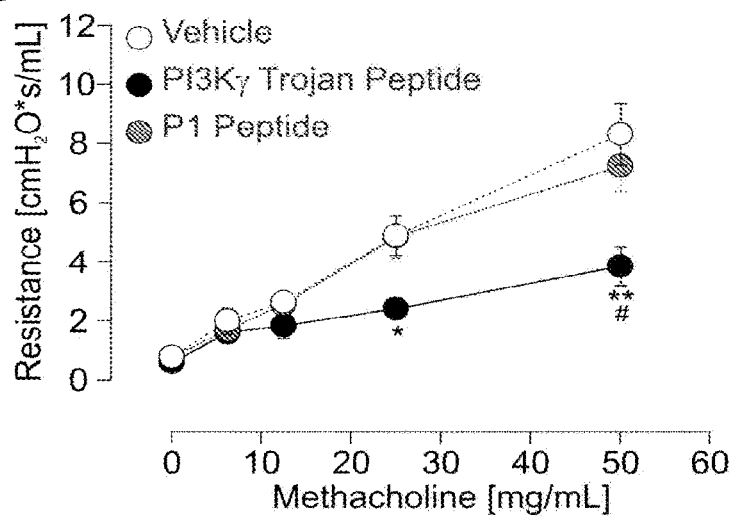
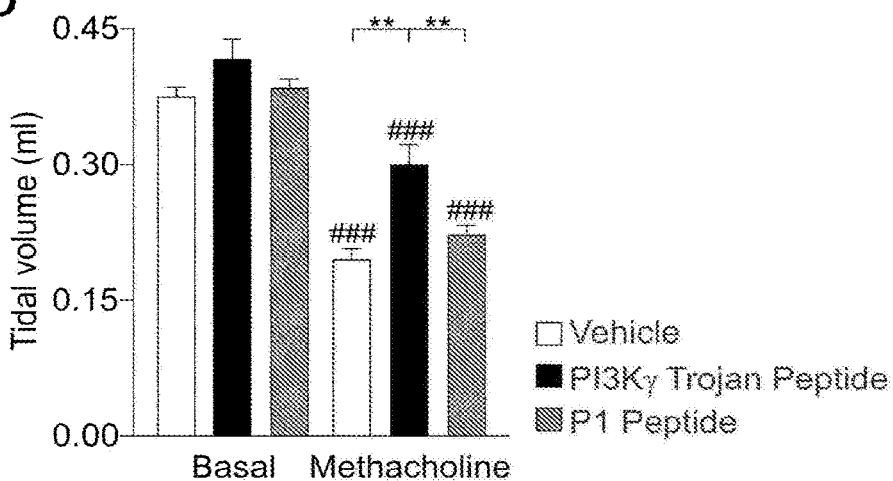

Figure 4
A
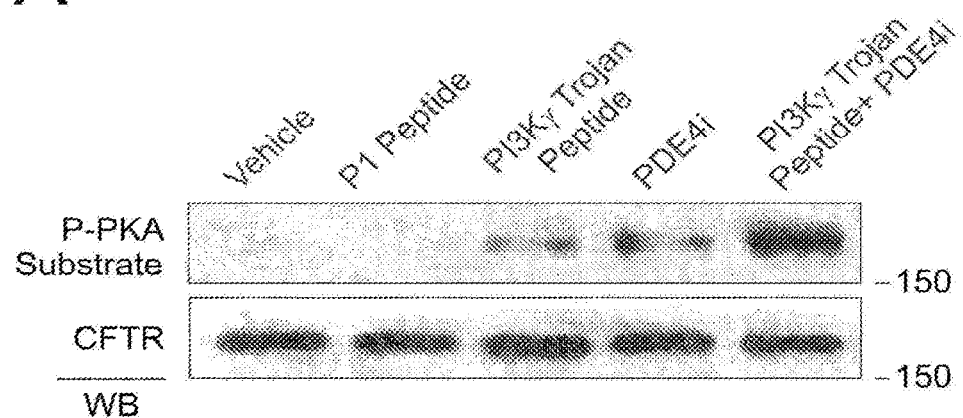
B
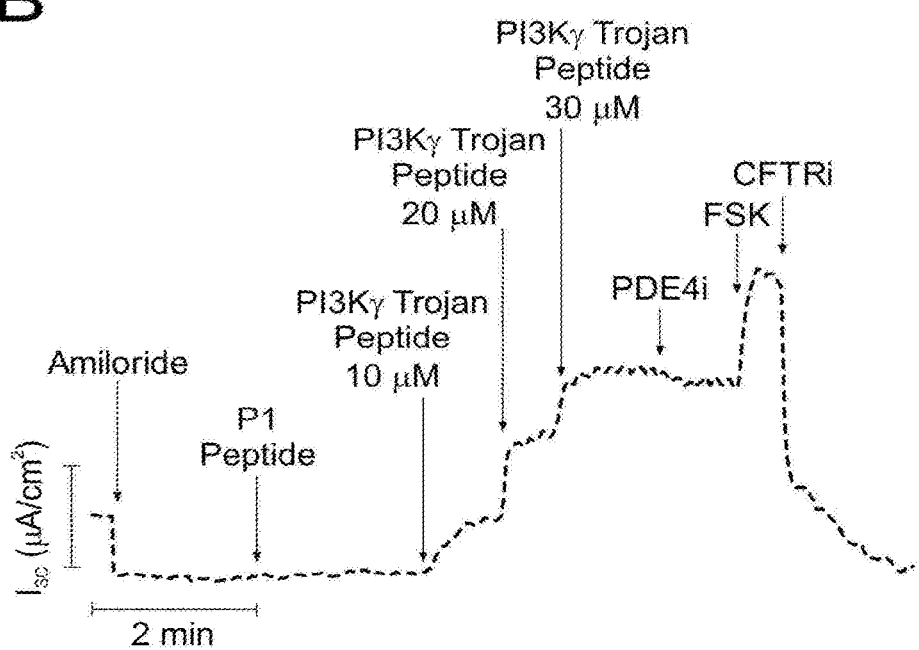

Figure 5
A
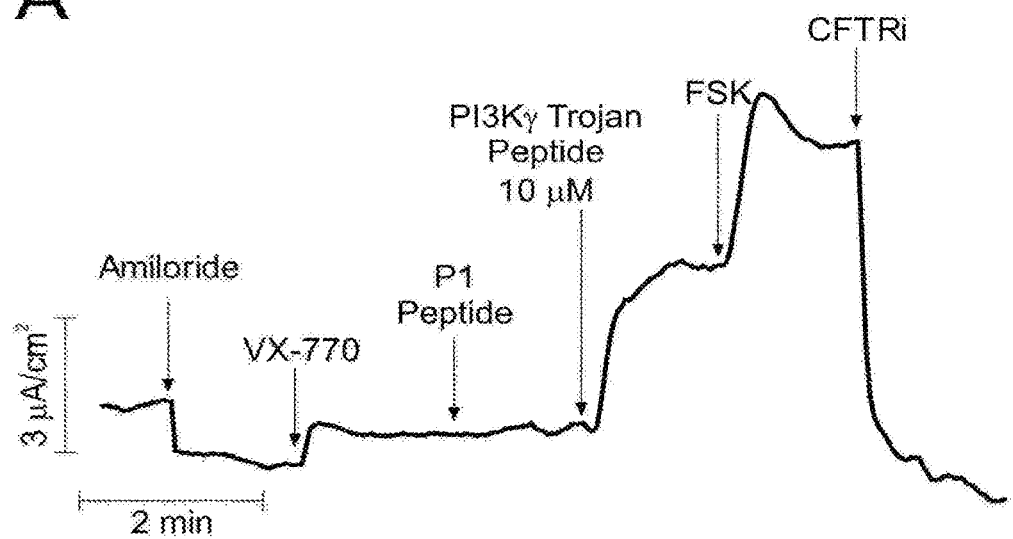
B
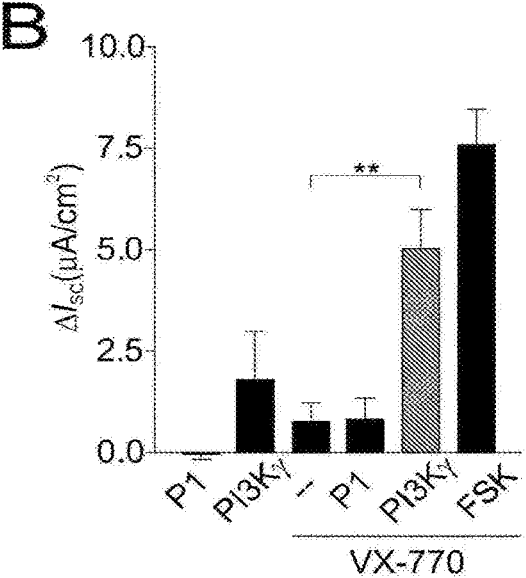

Figure 6

| Cell-penetrating polypeptides | Sequence | SEQ ID No. |
|---|---|---|
| Penetratin (pAntp) | RQIKIWFQNRRMKWKK | 3 |
| HIV TAT peptide | YGRKKRRQRRR | 4 |
| R7 peptide | RRRRRRR | 5 |
| KALA peptide | WEAKLAKALAKALAKHLAKALAKALKACEA | 6 |
| Buforin 2 | TRSSRAGLQFPVGRVHRLLRK | 7 |
| MAP | KLALKLALKALKAALKLA-amide | 8 |
| Transportan | GWTLNSAGYLLGKINLKALAALAKKIL-amide | 9 |
| Transportan 10 | AGYLLGKINLKALAALAKKIL-amide | 10 |
| pVEC | LLIILRRRIRKQAHAHSK-amide | 11 |
| MPG peptide | GALFLGWLGAAGSTMGAPKKKRKV-amide | 12 |

Figure 7
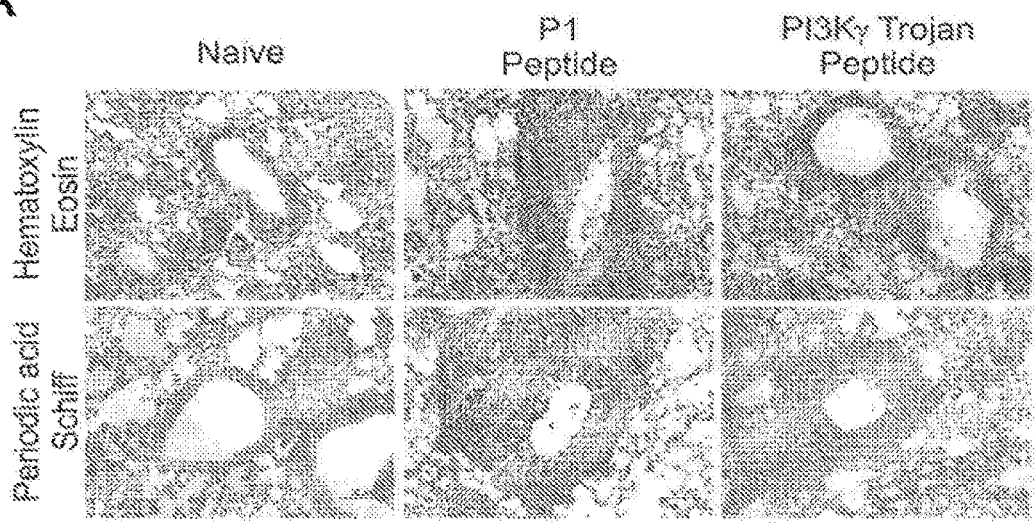
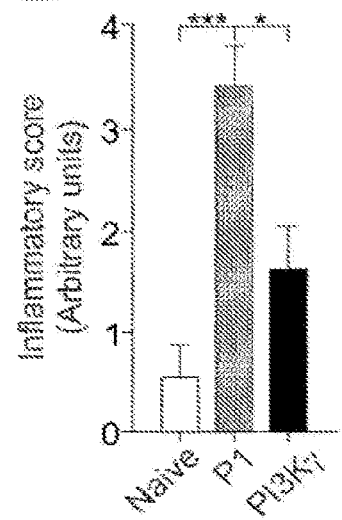 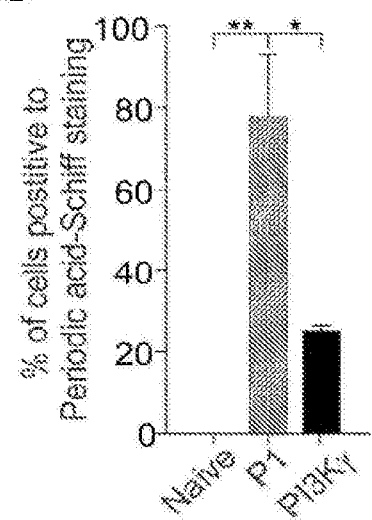

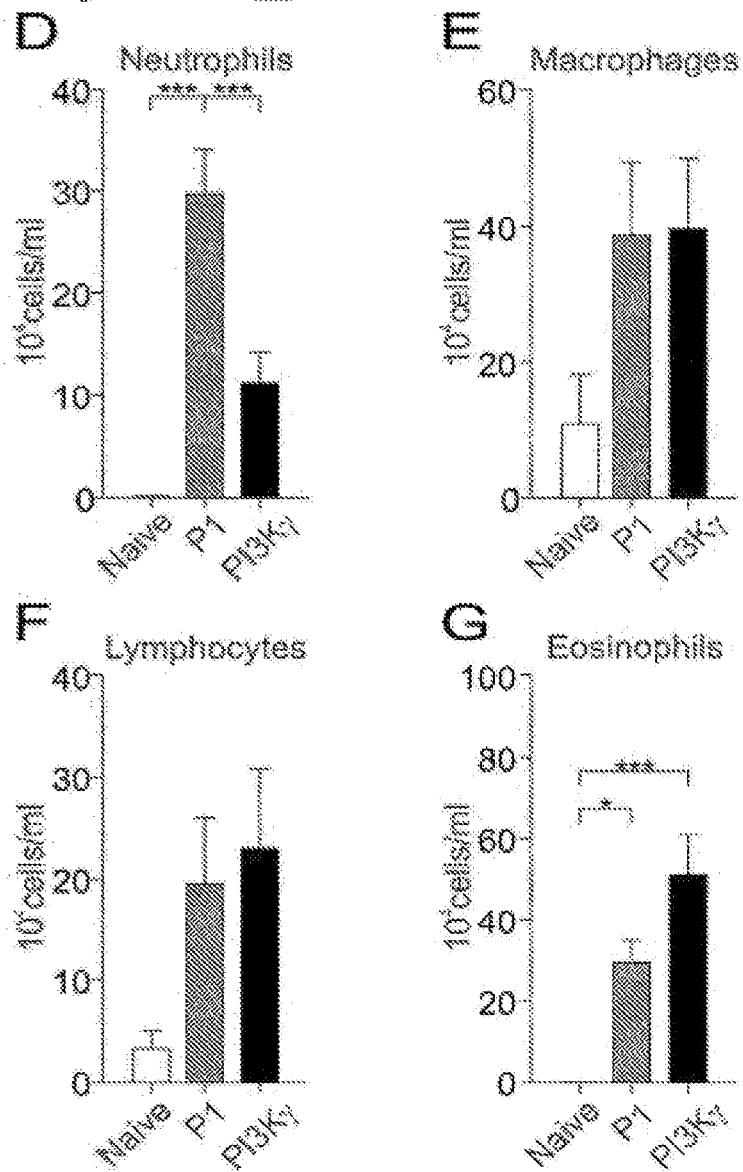

SEQUENCE LISTING

```
<160> NUMBER OF SEQ ID NOS: 13

<210> SEQ ID NO 1
<211> LENGTH: 25
<212> TYPE: PRT
<213> ORGANISM: homo sapiens

<400> SEQUENCE: 1

Lys Ala Thr His Arg Ser Pro Gly Gln Ile His Leu Val Gln Arg His
1               5                   10                  15

Pro Pro Ser Glu Glu Ser Gln Ala Phe
            20                  25

<210> SEQ ID NO 2
<211> LENGTH: 42
<212> TYPE: PRT
<213> ORGANISM: artificial
<220> FEATURE:
<223> OTHER INFORMATION: fusion peptide comprising SEQ ID No.:1 and SEQ
      ID No.:3

<400> SEQUENCE: 2

Arg Gln Ile Lys Ile Trp Phe Gln Asn Arg Arg Met Lys Trp Lys Lys
1               5                   10                  15

Gly Lys Ala Thr His Arg Ser Pro Gly Gln Ile His Leu Val Gln Arg
            20                  25                  30

His Pro Pro Ser Glu Glu Ser Gln Ala Phe
        35                  40
```

```
<210> SEQ ID NO 3
<211> LENGTH: 16
<212> TYPE: PRT
<213> ORGANISM: artificial
<220> FEATURE:
<223> OTHER INFORMATION: Antennapedia penetratin 1

<400> SEQUENCE: 3

Arg Gln Ile Lys Ile Trp Phe Gln Asn Arg Arg Met Lys Trp Lys Lys
1               5                   10                  15

<210> SEQ ID NO 4
<211> LENGTH: 11
<212> TYPE: PRT
<213> ORGANISM: artificial
<220> FEATURE:
<223> OTHER INFORMATION: HIV TAT peptide

<400> SEQUENCE: 4

Tyr Gly Arg Lys Lys Arg Arg Gln Arg Arg
1               5                   10

<210> SEQ ID NO 5
<211> LENGTH: 7
<212> TYPE: PRT
<213> ORGANISM: artificial
<220> FEATURE:
<223> OTHER INFORMATION: R7 peptide

<400> SEQUENCE: 5

Arg Arg Arg Arg Arg Arg Arg
1               5

<210> SEQ ID NO 6
<211> LENGTH: 30
<212> TYPE: PRT
<213> ORGANISM: artificial
<220> FEATURE:
<223> OTHER INFORMATION: KALA peptide

<400> SEQUENCE: 6

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30

<210> SEQ ID NO 7
<211> LENGTH: 21
<212> TYPE: PRT
<213> ORGANISM: artificial
<220> FEATURE:
<223> OTHER INFORMATION: Buforin 2

<400> SEQUENCE: 7

Thr Arg Ser Ser Arg Ala Gly Leu Gln Phe Pro Val Gly Arg Val His
1               5                   10                  15

Arg Leu Leu Arg Lys
            20

<210> SEQ ID NO 8
<211> LENGTH: 18
<212> TYPE: PRT
<213> ORGANISM: artificial
<220> FEATURE:
<223> OTHER INFORMATION: MAP
```

<400> SEQUENCE: 8

Lys Leu Ala Leu Lys Leu Ala Leu Lys Ala Leu Lys Ala Ala Leu Lys
1               5                   10                  15

Leu Ala

<210> SEQ ID NO 9
<211> LENGTH: 27
<212> TYPE: PRT
<213> ORGANISM: artificial
<220> FEATURE:
<223> OTHER INFORMATION: Transportan peptide

<400> SEQUENCE: 9

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 10
<211> LENGTH: 21
<212> TYPE: PRT
<213> ORGANISM: artificial
<220> FEATURE:
<223> OTHER INFORMATION: Transportan 10 peptide

<400> SEQUENCE: 10

Ala Gly Tyr Leu Leu Gly Lys Ile Asn Leu Lys Ala Leu Ala Ala Leu
1               5                   10                  15

Ala Lys Lys Ile Leu
            20

<210> SEQ ID NO 11
<211> LENGTH: 18
<212> TYPE: PRT
<213> ORGANISM: artificial
<220> FEATURE:
<223> OTHER INFORMATION: pVEC

<400> SEQUENCE: 11

Leu Leu Ile Ile Leu Arg Arg Arg Ile Arg Lys Gln Ala His Ala His
1               5                   10                  15

Ser Lys

<210> SEQ ID NO 12
<211> LENGTH: 24
<212> TYPE: PRT
<213> ORGANISM: artificial
<220> FEATURE:
<223> OTHER INFORMATION: MPG peptide

<400> SEQUENCE: 12

Gly Ala Leu Phe Leu Gly Trp Leu Gly Ala Ala Gly Ser Thr Met Gly
1               5                   10                  15

Ala Pro Lys Lys Lys Arg Lys Val
            20

<210> SEQ ID NO 13
<211> LENGTH: 3321
<212> TYPE: DNA
<213> ORGANISM: artificial
<220> FEATURE:
<223> OTHER INFORMATION: human PI3Kgamma cDNA

<400> SEQUENCE: 13

```
ggatccatgg agctggagaa ctataaacag cccgtggtgc tgagagagga caactgccga      60
aggcgccgga ggatgaagcc gcgcagtgct gcggccagcc tgtcctccat ggagctcatc     120
cccatcgagt tcgtgctgcc caccagccag cgcaaatgca agagcccga aacggcgctg     180
ctgcacgtgg ccggccacgg caacgtggag cagatgaagg cccaggtgtg gctgcgagcg     240
ctggagacca cgctggcggc ggacttctac caccggctgg accgcatca cttcctcctg     300
ctctatcaga agaaggggca gtggtacgag atctacgaca agtaccaggt ggtgcagact     360
ctggactgcc tgcgctactg gaaggccacg caccggagcc cgggccagat ccacctggtg     420
cagcggcacc cgccctccga ggagtcccaa gccttccagc ggcagctcac ggcgctgatt     480
ggctatgacg tcactgacgt cagcaacgtg cacgacgatg agctggagtt cacgcgccgt     540
ggcttggtga ccccgcgcat ggcggaggtg gccagccgcg accccaagct ctacgccatg     600
cacccgtggg tgacgtccaa gcccctcccg gagtacctgt ggaagaagat tgccaacaac     660
tgcatcttca tcgtcattca ccgcagcacc accagcagca ccattaaggt ctcacccgac     720
gacaccccg cgccatcct gcagagcttt tcaccaaga tggccaagaa gaaatctctg     780
atggatattc ccgaaagcca aagcgaacag gattttgtgc tgcgcgtctg tggccgggat     840
gagtacctgg tgggcgaaac gcccatcaaa aacttccagt gggtgaggca ctgcctcaag     900
aacggagaag agattcacgt ggtactggac acgcctccag acccggccct agacgaggtg     960
aggaaggaag agtggccact ggtggatgac tgcacgggag tcaccggcta ccatgagcag    1020
cttaccatcc acgcaaagga ccacgagagt gtgttcaccg tgtccctgtg ggactgcgac    1080
cgcaagttca gggtcaagat cagaggcatt gatatcccg tcctgcctcg gaacaccgac    1140
ctcacagttt ttgtagaggc aaacatccag catgggcaac aagtcctttg ccaaaggaga    1200
accagcccca aaccttcac agaggaggtg ctgtggaatg tgtggcttga gttcagtatc    1260
aaaatcaaag acttgcccaa aggggctcta ctgaacctcc agatctactg cggtaaagct    1320
ccagcactgt ccagcaaggc ctctgcagag tcccccagtt ctgagtccaa gggcaaagtt    1380
cagcttctct attatgtgaa cctgctgctg atagaccacc gtttcctcct cgccgtgga    1440
gaatacgtcc tccacatgtg gcagatatct gggaagggag aagaccaagg aagcttcaat    1500
gctgacaaac tcacgtctgc aactaaccca gacaaggaga actcaatgtc catctccatt    1560
cttctggaca attactgcca cccgatagcc ctgcctaagc atcagcccac ccctgacccg    1620
gaaggggacc gggttcgagc agaaatgccc aaccagcttc gcaagcaatt ggaggcgatc    1680
atagccactg atccacttaa ccctctcaca gcagaggaca agaattgct ctggcatttt    1740
agatacgaaa gccttaagca cccaaaagca tatcctaagc tatttagttc agtgaaatgg    1800
ggacagcaag aaattgtggc caaaacatac caattgttgg ccagaaggga gtctgggat    1860
caaagtgctt tggatgttgg gttaacaatg cagctcctgg actgcaactt ctcagatgaa    1920
aatgtaagag ccattgcagt tcagaaactg agagcttgg aggacgatga tgttctgcat    1980
taccttctac aattggtcca ggctgtgaaa tttgaaccat accatgatag cgcccttgcc    2040
agatttctgc tgaagcgtgg tttaagaaac aaaagaattg tcacttttt gttttggttc    2100
ttgagaagtg agatagccca gtccagacac tatcagcaga ggttcgctgt gattctggaa    2160
gcctatctga ggggctgtgg cacagccatg ctgcacgact ttacccaaca agtccaagta    2220
atcgagatgt tacaaaaagt caccccttgat attaaatcgc tctctgctga aaagtatgac    2280
gtcagttccc aagttatttc acaacttaaa caaaagcttg aaaacctgca gaattctcaa    2340
```

```
ctccccgaaa gctttagagt tccatatgat cctggactga aagcaggagc gctggcaatt    2400 gaaaatgta aagtaatggc ctccaagaaa aaaccactat ggcttgagtt taaatgtgcc     2460
gatcctacag ccctatcaaa tgaaacaatt ggaattatct ttaaacatgg tgatgatctg    2520
cgccaagaca tgcttatttt acagattcta cgaatcatgg agtctatttg ggagactgaa    2580
tctttggatc tatgcctcct gccatatggt tgcatttcaa ctggtgacaa aataggaatg    2640
atcgagattg tgaaagacgc cacgacaatt gccaaaattc agcaaagcac agtgggcaac    2700
acgggagcat ttaaagatga agtcctgaat cactggctca aagaaaaatc ccctactgaa    2760
gaaaagtttc aggcagcagt ggagagattt gtttattcct gtgcaggcta ctgtgtggca    2820
acctttgttc ttggaatagg cgacagacac aatgacaata ttatgatcac cgagacagga    2880
aacctatttc atattgactt cgggcacatt cttgggaatt acaaaagttt cctgggcatt    2940
aataaagaga gagtgccatt tgtgctaacc cctgacttcc tctttgtgat gggaacttct    3000
ggaaagaaga caagcccaca cttccagaaa tttcaggaca tctgtgttaa ggcttatcta    3060
gcccttcgtc atcacacaaa cctactgatc atcctgttct ccatgatgct gatgacagga    3120 atgcccagt taacaagcaa agaagacatt gaatatatcc gggatgccct cacagtgggg    3180
aaaaatgagg aggatgctaa aaagtatttt cttgatcaga tcgaagtttg cagagacaaa    3240
ggatggactg tgcagtttaa ttggtttcta catcttgttc ttggcatcaa acaaggagag    3300
aaacattcag cctaatctag a                                              3321
```

PI3K GAMMA INHIBITOR PEPTIDE FOR TREATMENT OF RESPIRATORY SYSTEM DISEASES

CROSS-REFERENCE TO RELATED APPLICATIONS

This application is a divisional of U.S. application Ser. No. 16/538,987 filed Aug. 13, 2019, which is a continuation of U.S. application Ser. No. 15/539,339 filed Jun. 23, 2017, which is the U.S. National Phase of International Application No. PCT/IB2015/059880, filed-Dec. 22, 2015, which designated the U.S. and claims priority to Italian Patent Application No. TO2014A001105, filed Dec. 24, 2014, the entire contents of each of which are hereby incorporated by reference.

REFERENCE TO SEQUENCE LISTING SUBMITTED ELECTRONICALLY

The content of the electronically submitted sequence listing (Name: (4636_0464_Sequence_Listing.txt; Size: 8.12 kilobytes; and Date of Creation: Jun. 25, 2020) filed with the application is incorporated herein by reference in its entirety.

FIELD OF THE INVENTION

The present description relates to a novel peptide inhibitor of PI3Kγ for the treatment of pathologies of the respiratory apparatus.

BACKGROUND OF THE INVENTION

Asthma is a chronic respiratory disease characterized by inflammation, airway hyperresponsiveness (AHR) and mucosal edema, which together lead to episodic bronchoconstriction and obstruction of the airways. The effectiveness of current anti-asthmatic treatments is unsatisfactory, and asthma remains an unresolved global issue.

The tone of the musculature of the airways is determined by a delicate balance between activation of the pro-contractile and pro-relaxation signaling pathways in smooth muscle cells. Contraction is primarily triggered by acetylcholine, the main parasympathetic neurotransmitter in the airways, which activates M3 muscarinic receptors, leading to mobilization of intracellular and extracellular calcium ($Ca^{2+}$). Conversely, relaxation of the airways is achieved by catecholamine-mediated activation of $β_2$-adrenergic receptors ($β_2$-AR), which promote the production of cyclic AMP (cAMP) and the consequent modulation of key effectors of $Ca^{2+}$ homeostasis. According to the pro-relaxing action of cAMP, agonists of $β_2$-ARs provide symptomatic relief of bronchospasms in patients with asthma. However, their effectiveness is limited in time, mainly due to the desensitization of $β_2$-ARs that occurs after repeated exposure to agonists. Similarly, inhibiting cAMP degradation by inhibitors of phosphodiesterase 4 (PDE4), the main enzymes responsible for cAMP hydrolysis in the airways, has been clinically tested, but displays unacceptable side effects, such as vomiting, nausea, diarrhea and weight loss, due to non-selective inhibition of PDE4 in the central nervous system.

Therefore, identifying new enzymes that regulate cAMP homeostasis, as well as novel strategies for manipulating the $β_2$-AR/cAMP signal transduction pathway in smooth muscle cells is desirable for treating respiratory diseases. Moreover, the same approach could also be used for therapeutic purposes in other pathological contexts, such as cystic fibrosis, where it is necessary to increase the levels of cAMP in the epithelial cells of the airways.

In the respiratory epithelium, the production of cAMP downstream of $β_2$-ARs is necessary to ensure the opening of the cAMP-dependent chloride channel (cystic fibrosis transmembrane conductance regulator, CFTR). Mutations in the gene that encodes for this protein are the main cause of cystic fibrosis (CF). Among these, deletion of phenylalanine 508 (ΔF508) constitutes the most common alteration in CF patients and leads to defects in both membrane expression and opening of the channel. A number of CFTR corrector and potentiator drugs, which rescue the membrane expression and the cAMP-mediated opening of the channel, respectively, have been developed, but their effectiveness is unsatisfactory. In particular, CFTR potentiators require high concentrations of intracellular cAMP to be effective. Therefore, drugs that are able to stimulate cAMP levels may constitute novel strategies to increase the effectiveness of currently available treatments, or to directly correct functional defects of CFTR in CF.

Previous studies have shown that phosphoinositide 3-kinase γ (PI3Kγ) controls the compartmentalization of cAMP downstream of $β_2$-AR. In cardiomyocytes, PI3Kγ acts as an anchor protein (AKAP) (1), which binds protein kinase A (PKA) to several isoforms of PDE3 and PDE4. PI3Kγ-associated PKA in turn phosphorylates and promotes the activation of the PDEs and the consequent reduction of cAMP downstream of $β_2$-ARs, ultimately limiting the arrhythmogenic release of $Ca^{2+}$ (2). Although several inhibitors of the kinase activity of PI3Kγ have been developed, there are currently no methods for selectively interfering with the adaptor or anchor protein activity of PI3Kγ.

SUMMARY OF THE INVENTION

Bearing in mind these premises, there is therefore a need for improved and more effective solutions for treating diseases of the respiratory system compared to the known therapies.

In accordance with the invention, the aforesaid object is achieved thanks to the solution specifically recalled in the attached claims, which constitute an integral part of the present description.

One embodiment of the present invention relates to a fusion peptide comprising:

i) an amino acid sequence as defined in SEQ ID No.: 1 or a related homolog having at least 90% identity with SEQ ID No.: 1, and having the ability of the sequence SEQ ID No.: 1 to inhibit the kinase-independent function of PI3Kγ, and ii) a peptide having the ability to penetrate a cell, for use as a medicament, in particular for treating respiratory diseases.

A different embodiment of the present invention concerns a product comprising i) a fusion peptide as defined above and ii) a potentiator of the cystic fibrosis transmembrane conductance regulator (CFTR) and/or a corrector of the cystic fibrosis transmembrane conductance regulator (CFTR), as a combined preparation for sequential, simultaneous or separate use for treating respiratory diseases, preferably cystic fibrosis.

The present description provides in vitro and in vivo experimental evidence of the efficacy of treating pathologies of the respiratory system by means of administering a fusion peptide comprising residues 126-150 of human PI3Kγ (SEQ ID No.: 1) or its homologs. The fusion peptide of the present description is, in fact, able to inhibit the interaction between PKA and PI3Kγ and to consequently reduce the activity of the PDEs associated with PI3Kγ, increasing cAMP levels and reducing the entry of $Ca^{2+}$ through voltage-operated calcium channels (VOCCs). Furthermore, the fusion peptide described here increases cAMP levels in vivo in the airways and functions as a bronchodilator when administered by an intra-tracheal route to healthy and asthmatic mice. Finally, the fusion peptide carries out the function of CFTR potentiator, increasing cAMP and thereby enhancing the conductance to chloride (Cl⁻) of CFTR in bronchial epithelial cell lines expressing wild-type or a ΔF508 mutant CFTR, which is the most frequent mutation in patients with cystic fibrosis.

BRIEF DESCRIPTION OF THE DRAWINGS

The invention will now be described in detail, purely by way of illustrative and non-limiting example, with reference to the attached figures, wherein:

FIG. 1. A Trojan peptide derived from PI3Kγ inhibits the activity of PDEs and enhances $β_2$-AR/cAMP signaling in smooth muscle cells of the airways. A) Schematic representation of the PI3Kγ inhibitory peptide permeable to cell membranes. The 126-150 region of human PI3Kγ was fused with the sequence of Penetratin 1 of Antennapedia. B) Intracellular localization of the PI3Kγ inhibitory Trojan peptide. hBSMCs were incubated with the peptide labeled with fluorescein (FITC, 50 μM) and the intracellular fluorescence was analyzed after 30 minutes from the beginning of the treatment. Filamentous actin staining (left panels) and FITC fluorescence (middle panels) with relative magnification (right panels) are presented. C) Phosphodiesterase activity precipitated by anti-PDE4B and anti-PDE4D antibodies in smooth muscle cells of trachea isolated from $PI3Kγ^{+/+}$ and $PI3Kγ^{-/-}$ animals and treated with either vehicle or the PI3Kγ inhibitory Trojan peptide (50 μM, 30 minutes; n≥4 independent experiments). D) hBSMCs were transfected with the FRET probe for cAMP, ICUE3, and pre-treated with either vehicle, PI3Kγ inhibitory peptide or Penetratin 1 control peptide (50 μM, 30 minutes) before activation of $β_2$-ARs with isoproterenol (ISO; 100 nM) and the selective antagonist of $β_1$-AR, CGP-20712A (CGP, 100 nM). Representative FRET traces of n≥3 independent experiments are presented. E) Maximum change in FRET signal (%) of the curves as measured in D. *P<0.05, P<0.01, *P<0.001 by one-way ANOVA followed by Bonferroni test.

FIG. 2. The PI3Kγ inhibitory Trojan peptide inhibits calcium entry through the L-type channel in human smooth muscle cells of the airways. A) Representative traces of Ca transients recorded in hBSMCs pre-treated with vehicle, PI3Kγ inhibitory Trojan peptide or P1 control peptide (50 μM, 30 minutes) prior to stimulation with the muscarinic agonist carbachol (Carb, 10 μM, top panel) and a depolarizing solution (40 mM KCl, bottom panel). B) Maximum change of the fluorescence ratio of the indicator INDO-1 (AU) of the $Ca^{2+}$ transients shown in A. C) cAMP-dependent phosphorylation of the $Ca_v1.2$ subunit (Ser-1928) of the L-type calcium channel (LTCC) in hBSMCs treated with the PI3Kγ inhibitory Trojan peptide or P1 control peptide (50 μM, 30 minutes). Representative images and relative quantification of n≥3 independent Western blot experiments are shown. P<0.01 and *P<0.001 by one-way ANOVA followed by the Bonferroni test.

FIG. 3. The PI3Kγ inhibitory Trojan peptide increases cAMP levels in the airways in vivo, and attenuates airway hyperresponsiveness in healthy and asthmatic mice. A) The PI3Kγ inhibitory Trojan peptide was labeled with FITC and administered via the intra-tracheal route to mice of the BALC/c strain (1.5 μg/mouse). The fluorescence in the lung and trachea was analyzed by confocal microscopy at 30 minutes after treatment. Control mice were instilled with an equal volume of solution used for FITC labeling. FITC fluorescence images of sections of trachea, lungs, brain and myocardium of animals treated with vehicle (upper panels) or with the PI3Kγ inhibitory Trojan peptide (lower panels) are presented. B) cAMP levels in the whole trachea (left panel) and the lungs (right panel) of mice treated as described in A. *P<0.05 and **P<0.01 by one-way ANOVA followed by Bonferroni test. C) Airway hyperreactivity was measured as average resistance of the lung in healthy mice, anesthetized and ventilated, treated with a spray of vehicle, PI3Kγ inhibitory Trojan peptide (1.5 μg) or P1 control peptide (equimolar amount) before exposure to increasing doses of methacholine. *P<0.05 and P<0.01 compared to the vehicle; # P<0.05 versus P1 by two-way ANOVA followed by Bonferroni test. D) Airway hyperresponsiveness was measured as change in tidal volume in asthmatic mice, anesthetized and ventilated, in response to methacholine (500 mg/kg, intravenously administered). Animals sensitized to ovalbumin were treated with vehicle, the PI3Kγ inhibitory Trojan peptide (150 μg) or P1 control peptide (equimolar amount) for 30 minutes before administering methacholine. P<0.01 versus the vehicle and the control peptide; ### P<0.001 versus baseline using two-way ANOVA followed by Bonferroni test.

FIG. 4. The Trojan peptide derived from PI3Kγ increases cAMP-dependent phosphorylation and chloride conductance of wild-type CFTR. A) cAMP-mediated phosphorylation of CFTR in human airway epithelial cells (NuLi-1) treated with vehicle (lane 1), P1 control peptide (25 μM, lane 2), PI3Kγ inhibitory Trojan peptide (25 μM, lane 3), PDE4 inhibitor Rolipram alone (PDE4i; 10 μM, lane 4) or together with the Trojan peptide derived from PI3Kγ (lane 5) for 30 minutes. Representative images of Western Blot detection of CFTR immunoprecipitations and phosphorylation by PKA of n≥3 independent experiments are shown. B) Representative trace of CFTR currents measured in Ussing chambers in cultures of NuLi-1 cells. The following treatments were applied at the indicated times: amiloride (inhibitor of the ENAC channel, 10 μM), P1 control peptide (30 μM), increasing concentrations of the Trojan peptide derived from PI3Kγ (10 μM, 20 μM and 30 μM), PDE4 inhibitor Rolipram (PDE4i; 10 μM), forskolin (FSK, 10 μM) and CFTR inhibitor 172 (CFTRi; 20 μM).

FIG. 5. The Trojan peptide derived from PI3Kγ increases the conductance of CFTR in airway epithelial cells with ΔF508 mutation. A) Representative trace of CFTR currents measured in Ussing chambers in cultures of airway epithelial cells with ΔF508 mutation (CuFi-1), treated with the corrector VX-809 (20 μM; 24 hours). The following treatments were applied at the indicated times: amiloride (inhibitor of the ENAC channel, 10 μM), CFTR potentiator VX-770 (10 μM), P1 control peptide (10 μM), PI3Kγ inhibitory Trojan peptide (10 μM), forskolin (FSK, 10 μM) and CFTR inhibitor 172 (CFTRi; 20 μM). B) Average current variations in response to the indicated treatments. **P<0.01 by one-way ANOVA followed by Bonferroni test.

FIG. 6. Sequences of penetrating polypeptides suitable for producing fusion peptides of the present description.

FIG. 7. The PI3Kγ-derived Trojan peptide reduces lung inflammation in asthmatic mice. A) Representative images of hematoxylin-eosin (top images) and periodic acid-Schiff's reagent (bottom images) staining of lung sections of naïve mice or mice sensitized with ovalbumin and pre-treated with the Trojan peptide derived from PI3Kγ (25 µg/mouse/injection) or with P1 control peptide (equimolar amounts), before each intranasal administration of ovalbumin. Sections were stained with hematoxylin-eosin for analyzing the tissue morphology and the level of inflammation, and with periodic acid-Schiff's reagent to determine the presence of goblet cells. B) Semi-quantitative analysis of the degree of peribronchial inflammation in lung sections as shown in A). C) Percentage of epithelial cells positive to the staining with periodic acid-Schiff's reagent in the epithelium of lung sections as shown in A). D-G) Number of neutrophils (D), macrophages (E), lymphocytes (F) and eosinophils (G) in the bronchoalveolar lavage of mice pre-treated with the Trojan peptide derived from PI3Kγ or P1 control peptide as described in A). *P<0.05, P<0.01 and *P<0.001 by one-way ANOVA followed by Bonferroni test.

DETAILED DESCRIPTION OF THE INVENTION

The invention will now be described in detail, purely by way of illustrative and non-limiting example, with reference to the single drawing in which an extraction system under pressure usable for the purposes of implementing the method described herein is schematically represented.

In the following description, numerous specific details are presented to provide a thorough understanding of the embodiments. The embodiments may be implemented in practice without one or more of the specific details, or with other methods, components, materials, etc. In other cases, well-known structures, materials, or operations are not shown or described in detail to avoid obscuring certain aspects of the embodiments.

Throughout the present specification, the reference to "one embodiment" or "embodiment" means that a specific feature, structure, or characteristic described in connection with the embodiment is included in at least one embodiment. Therefore, the appearance of expressions "in a certain embodiment" or "in an embodiment" in various sites throughout the present specification does not necessarily always refer to the same embodiment. Furthermore, the particular features, structures, or characteristics may be combined in any suitable manner in one or more embodiments.

The titles used here serve merely for convenience and do not interpret the object or meaning of the embodiments.

One embodiment of the present description relates to a fusion peptide comprising: i) an amino acid sequence as defined in SEQ ID No.: 1 or a related homolog having at least 90% identity with SEQ ID No.: 1, and having the ability of the sequence SEQ ID No.: 1 to inhibit the kinase-independent function of PI3Kγ, and ii) a peptide having the ability to penetrate a cell, for use as a medicament, in particular for treating respiratory diseases.

A different embodiment of the present invention concerns a product comprising i) a fusion peptide as defined above and ii) a potentiator of the cystic fibrosis transmembrane conductance regulator and/or a corrector of the cystic fibrosis transmembrane conductance regulator (CFTR), as a combined preparation for sequential, simultaneous or separate use for treating respiratory diseases, preferably cystic fibrosis.

The use of a product comprising a fusion peptide as defined above, a corrector of the cystic fibrosis transmembrane conductance regulator (CFTR) and a potentiator of the cystic fibrosis transmembrane conductance regulator (CFTR) as a combined preparation for sequential, simultaneous or separate use is particularly suitable for treating patients with cystic fibrosis who carry the ΔF508 mutation of CFTR.

The present description concerns the production and the therapeutic applications of a fusion peptide permeable to cell membranes, which inhibits the interaction between PI3Kγ and the activator of PDE, PKA. The fusion peptide of the present description reduces the activity of specific PDE, enhancing the signaling of the $β_2$-AR/cAMP signal transduction pathway and producing cAMP-mediated pro-relaxing effects, both in smooth muscle cells of human airways and in vivo, in a preclinical model of allergic asthma. Furthermore, the fusion peptide with PI3Kγ inhibitory activity enhances the same signaling pathway in epithelial cells of the respiratory tract and stimulates the cAMP-dependent opening of the wild type CFTR channel (whose nucleotide and amino acid sequences are available in the GenBank sequence database as access numbers NM_000492.3 and NP_000483.3, respectively) and of CFTR with the ΔF508 mutation (the sequence of this mutation is available in the GenBank sequence database as access number S64640.1), which is the main cause of cystic fibrosis.

Overall, the results shown here demonstrate the possibility of using the fusion peptide or homologs thereof, having the ability to inhibit PI3Kγ, as a local therapy by inhalation, for treating respiratory diseases such as allergic asthma and cystic fibrosis.

Although in the last decade numerous inhibitors of the kinase activity of PI3Kγ have been developed, many of which are currently in clinical development for treating neoplastic diseases, there are no methods that allow selective interference with the kinase-independent activity, or rather with the PKA- or AKAP-anchoring protein, of the enzyme.

It has been previously shown that a peptide which comprises the binding site of PI3Kγ to PKA, consisting of residues 126-150 of human PI3Kγ, displaces the interaction between the two proteins and reduces the activity of the PI3Kγ-bound PDE, PDE3B, in in vitro interaction studies (1).

The present description shows, in a completely unexpected way, that the PI3Kγ 126-150 peptide (SEQ ID No.: 1-KATHRSPGQIHLVQRHPPSEESQAF) conjugated to a peptide permeable to cell membranes, such as, for example, the Penetratin 1 of Antennapedia (SEQ ID No.: 3) (3), can be used as an inhibitor of the kinase-independent function of PI3Kγ in vivo. The PI3Kγ inhibitory fusion peptide penetrates smooth muscle cells of the airways and enhances the $β_2$-AR/cAMP signaling pathway. In particular, the data show that the fusion peptide increases cAMP levels and limits airway hyperresponsiveness in a preclinical model of allergic asthma and that it efficiently reaches the lower respiratory tract when administered locally by the intratracheal route. These data therefore demonstrate the clinical use of a PI3Kγ inhibitory fusion peptide in aerosol therapy for treating respiratory diseases.

The current inhalation therapy for bronco-obstructive diseases is based on the use of $β_2$-AR agonists, such as salbutamol and formoterol and of PDE4 inhibitors, such as Roflumilast, which was recently approved for treating chronic obstructive pulmonary disease (COPD).

Although acute treatment with β-AR agonists produces evident clinical benefits, chronic or repeated exposure to these drugs may result in a significant reduction and/or complete loss of their effectiveness in asthmatic patients, due to the agonist-dependent desensitization of membrane β-ARs.

The present description provides a solution to this problem and proposes the use of an inhibitory peptide that affects the activity of the enzyme PI3Kγ and, as such, does not act directly on the stimulation of $@_2$-AR, but enhances the cascade of downstream signaling events. In this way, a PI3Kγ inhibitory peptide offers the unique opportunity to modulate $β_2$-AR-dependent cAMP domains, ensuring broncho-relaxing effects similar to those mediated by $β_2$-AR agonists, without inducing receptor inactivation.

The data provided herein demonstrate that inhibiting the PKA-anchoring function of PI3Kγ only reduces the PDE activity in cells expressing PI3Kγ (PI3Kγ$^{+/+}$), but not in cells lacking the enzyme (PI3Kγ$^{-/-}$), thus indicating that the fusion peptide of the present description inhibits the PDEs exclusively regulated by PI3Kγ.

The PI3Kγ inhibitory peptide therefore represents a unique tool that ensures isoform-selective inhibition of PDEs and allows limiting the major side effects that are associated with non-selective inhibitors of PDE4, such as Roflumilast, arising mainly from inhibition of isoforms that are not expressed in the respiratory system.

Although PDE4 inhibitors are characterized by important pro-relaxant effects in isolated cells, they are not optimal bronchodilators in vivo, where they mainly exert anti-inflammatory functions.

The results provided herein demonstrate that the fusion peptide with the ability to inhibit the kinase-independent function of PI3Kγ, subject of the present description, has a strong bronchodilator function in vivo, in healthy animals and in a pre-clinical model of allergic asthma. These effects can be explained by the ability of the peptide to interfere with the catalytic activity of multiple PDE isoforms, not only including PDE4, but also PDE3.

In agreement with the present data, it has been shown that inhibiting PDE3 and PDE4 can be additive or synergistic. In particular, PDE4 and PDE3 inhibitors are ineffective if used alone, but act synergistically in inhibiting smooth muscle contraction. Therefore, inhibiting the kinase-independent activity of PI3Kγ provides a unique tool to simultaneously inhibit specific isoforms of PDE3 and PDE4, in particular those critically involved in regulating the contractility of the bronchial smooth muscle.

Since PDE3 and PDE4 are not only expressed in the airways, but also in the myocardium and the central nervous system, systemic inhibition of even selected isoenzymes can cause major side effects. In particular, the inhibition of PDE3 and PDE4 in vivo may have pro-arrhythmogenic, pro-emetic and pro-anorexigenic effects.

The present description shows that the fusion peptide having the ability to inhibit the kinase-independent activity of PI3Kγ is therapeutically effective, and that an aerosol formulation of the PI3Kγ inhibitory peptide is distributed efficiently in the lower respiratory tract. Furthermore, the use of a peptide molecule provides a broader therapeutic effect/side effect profile compared to small molecules, such as PDE inhibitors, which can diffuse rapidly to other tissues outside of the respiratory system.

The data provided herein demonstrate that a fluorescent version of the PI3Kγ inhibitory peptide accumulates in the trachea and lungs following intra-tracheal administration, without reaching the myocardium and the brain.

On the basis of these data, it is therefore possible to conclude that an inhalation therapy based on a peptide, permeable to cell membranes, which selectively inhibits the kinase-independent activity of the PI3Kγ enzyme, is highly effective. This therapeutic approach can be used for treating different respiratory diseases, from asthma to cystic fibrosis, where agents able to increase intracellular cAMP downstream of $β_2$-ARs are necessary.

The results presented here demonstrate that the PI3Kγ inhibitory peptide not only increases cAMP levels in smooth muscle, but also in the epithelial compartment of the airways, thus opening up the possibility of exploiting this compound to also stimulate the cAMP-mediated opening of the CFTR channel, which is defective in patients with cystic fibrosis.

The data provided here also show that inhibition of PI3Kγ acts synergistically with a known, clinically advanced, CFTR potentiator, VX-770, by increasing the conductance of one of the most common mutated forms of CFTR in cystic fibrosis. These data demonstrate, for the first time, the ability of a PI3Kγ-inhibiting molecule to increase the activity of a known CFTR potentiator, VX-770, which is known to stimulate the conductance of different mutant forms of CFTR, with the exception of the most common mutant in cystic fibrosis, ΔF508.

The fusion peptide of the present description may therefore be used in combination with a potentiator of cystic fibrosis transmembrane conductance regulator (CFTR) and/or a corrector of the cystic fibrosis transmembrane conductance regulator (CFTR), as a combined preparation for the sequential, simultaneous or separate use in treating respiratory diseases characterized by a defective cAMP-mediated opening of CFTR, such as in patients with cystic fibrosis.

The combined use of a potentiator of the cystic fibrosis transmembrane conductance regulator (CFTR), and a corrector of the cystic fibrosis transmembrane conductance regulator (CFTR), together with the fusion peptide of the present description, is particularly suitable for treating cystic fibrosis patients carrying the ΔF508 CFTR mutation, to whom administration of a CFTR corrector is necessary to allow the expression of mutant CFTR at the membrane.

Potentiators of the cystic fibrosis transmembrane conductance regulator (CFTR), which can be advantageously used in combination with the fusion peptide of the present description are, for example: Ivacaftor or VX-770 (N-(2,4-Di-tert-butyl-5-hydroxyphenyl)-1,4-dihydro-4-ossoquinoline-3-carboxamide) and VX-532 (4-Methyl-2-(5-phenyl-1H-pyrazol-3-yl)-phenol).

Correctors of the cystic fibrosis transmembrane conductance regulator (CFTR), which can be advantageously used in combination with the fusion peptide of the present description and with a potentiator of the cystic fibrosis transmembrane conductance regulator (CFTR) are for example: VX-809 (3-(6-(1-(2,2-difluorobenzo[d][1,3]dioxol-5yl)cyclopropanecarboxamido)-3-methylpyridin-2-yl) benzoic acid) and VX-661 ((R)-1-(2,2-difluorobenzo [(d][1,3]dioxol-5-yl)-N-(1-(2,3-dihydroxypropyl)-6-fluoro-2-(1-hydroxy-2 methylpropan-2-yl)-1H-indol-5-yl)cyclopropanecarboxamide).

Overall, this study demonstrates the therapeutic potential of a fusion peptide that selectively inhibits the kinase-independent activity of PI3Kγ.

The molecule can be used for treating respiratory diseases, including allergic asthma, where drugs designed to increase intracellular levels of cAMP and to promote relaxation of bronchial smooth muscle are highly desirable.

In addition, this compound can be applied to patients with cystic fibrosis where agents that elevate cAMP concentrations are key tools to stimulate cAMP-mediated opening of defective CFTR.

Furthermore, peptide-mediated inhibition of PI3Kγ can be applied to all pathological conditions characterized by a hypo-functional CFTR, including COPD, where the exposure to cigarette smoke has been demonstrated to alter the activity of CFTR.

Finally, through the functional block of PDE4, the fusion peptide of the present description having the ability to inhibit PI3Kγ is capable of exerting important anti-inflammatory actions. The experimental evidence reported here demonstrates that the peptide indeed limits the peribronchial inflammation associated with allergic asthma. It is therefore evident that inhibiting the kinase-independent activity of PI3Kγ can provide multiple independent therapeutic benefits in treating respiratory diseases, acting at the same time as a bronchodilator, CFTR potentiator and anti-inflammatory agent.

Below, the invention will be described in detail, by way of non-limiting example, with reference to a fusion peptide having the sequence shown in SEQ ID No.: 2 (hereinafter also referred to as "Trojan peptide derived from PI3Kγ"), comprising the amino acid sequence SEQ ID No.: 1 and a peptide penetrating the cell corresponding to the Penetratin 1 of Antennapedia (SEQ ID No.: 3, described in (3)).

It is clear that the scope of this description is not in any way limited to the specific sequence of the fusion peptide of SEQ ID No.: 2, since the fusion peptide of the present description can comprise i) sequences having a homology with SEQ ID No.: 1 of at least 90% and having the ability of SEQ ID No.: 1 to inhibit the kinase-independent function of PI3Kγ and ii) sequences of a peptide penetrating the cell, for example, selected from the polypeptide HIV-TAT, Antennapedia homeodomain peptides, also known as penetrating peptides or pAntp, R7 peptide, KALA peptide, buforin 2, MAP, transportan, transportan 10, pVEC, or MPG peptide. The sequences corresponding to the polypeptides penetrating the cells mentioned above are shown in FIG. 6 and specified in SEQ ID No.: 3 to 12.

Moreover, in producing the Trojan peptide derived from PI3Kγ, the peptide having the ability to penetrate the cell was fused to the N-terminus of SEQ ID No.: 1. It is, however, possible to produce a fusion peptide that falls within the scope of the present description by creating a fusion of the peptide having the ability to penetrate the cell at the C-terminus of the SEQ ID No.: 1.

Materials and Methods

Determining the Ability of a Peptide Homologous to SEQ ID No.: 1 to Inhibit the Kinase-Independent Function of PI3Kγ

To determine the ability of a homolog peptide, having at least 90% identity with SEQ ID No.: 1, to inhibit the function of AKAP of PI3Kγ, a previously-described competition assay was used (1). The homolog peptide was re-suspended in phosphate-buffered saline solution (PBS) to a final concentration of 50 μM or 250 μM. HEK293 cells (ATCC Number: CRL-1573™) were transfected, using the calcium phosphate method, with a construct made of the expression vector pcDNA3.1 (Life Technologies, Carlsbad, Calif., USA; product code V790-20), in which human PI3Kγ cDNA was cloned (SEQ ID No.: 13) using the restriction enzymes BamHI and XbaI (New England Biolabs, Ipswich, Mass., USA). The pcDNA3.1-PI3Kγ construct is freely available from Dr. Emilio Hirsch at the University of Turin, Turin, ITALY.

At 48 hours following transfection, cells were lysed in cold lysis buffer containing 120 mmol/L NaCl, 50 mmol/L Tris-HCl (pH 8.0), complete protease inhibitors (Roche Applied Science, Indianapolis, Ind.) and phosphatase inhibitors (50 mmol/L sodium fluoride, 1 mmol/L sodium orthovanadate and 10 mmol/L sodium pyrophosphate). After 30 min of incubation on ice, lysates were centrifuged at 13000 rpm for 10 min at 4° C. and the supernatant was incubated with the peptide for 30 minutes at room temperature. After incubation, the regulatory subunit of PKA (PKA RII) was immunoprecipitated by incubating the protein extract with 30 μL of a 1:1 mixture of Protein A and Sepharose (Amersham Biosciences, Buckinghamshire, UK) and an anti-PKA RII C20 antibody (Santa Cruz Biotechnology Inc., Dallas, Tex., USA; product code: sc-908) for 2 h at 4° C., with shaking. Immune complexes were washed extensively with lysis buffer and the association of PI3Kγ with PKA RII was analyzed by Western blot analysis using a monoclonal anti-PI3Kγ antibody (freely available from Dr. Emilio Hirsch at the University of Turin, Turin, Italy).

Animals

Knock-out mice for PI3Kγ (PI3Kγ$^{-/-}$) and knock-in mice expressing a catalytically-inactive form of PI3Kγ (PI3Kγ$^{KD/KD}$) were generated as previously described (4, 5). Mutant mice were crossed with animals of a C57Bl/6J genetic background for 15 generations and C57Bl/6J mice were used as controls (PI3Kγ1+). For studies of airway hyperresponsiveness in asthmatic and healthy mice, BALB/C female mice were used. For all experiments, animals between the ages of 8 and 12 weeks were used.

Mice were maintained in groups, with free access to food (standard diet) and water, in a controlled system which provides a cycle of 12 hours of light and 12 hours of darkness. Animals were used according to the guidelines and institutional regulations on animal welfare, approved by the local Animal Ethics Committee.

Cell Culture and Transfection

Human bronchial smooth muscle cells (hBSMCs) were purchased from Lonza (CC-2576, Lonza Walkersville, Inc. USA), grown in Dulbecco's Modified Eagle Medium (DMEM, Gibco, Carlsbad, Calif.), and supplemented with 10% fetal bovine serum (FBS) and 5 mM penicillin/streptomycin (Gibco, Carlsbad, Calif.). Cells up to passage 15 were used for experiments.

Human bronchial smooth muscle cells (hBSMCs) were transfected with a plasmid encoding the FRET probe for cAMP, ICUE3 (described in the U.S. Pat. No. 8,236,523 B2) (2), by electroporation with a Nucleofector device (AMAXA, Gaithersburg, Md.), according to the manufacturer's protocol. Briefly, 1×10$^6$ cells were re-suspended in 100 μL of nucleofection solution (VPI-1004, AMAXA, Gaithersburg, Md.), mixed with 1 μg of pcDNA3-ICUE3 (described in U.S. Pat. No. 8,236,523 B2), and subjected to electroporation in a nucleofection apparatus of Amaxa Biosystems (Program A-033). Live cell imaging experiments were performed at 24 hours after transfection.

Human airway epithelial cell lines expressing a wild-type CFTR (NuLi-1) or with the ΔF508 mutation (CuFi-1) were purchased from ATCC (NuLi-1 product code: ATCC® CRL-4011™; CuFi-1 product code: ATCC® CRL-4013™). Cells were cultured in Dulbecco's Modified Eagle Medium (DMEM, Gibco, Carlsbad, Calif.) supplemented with 10% fetal bovine serum (FBS), 30 μg/mL of penicillin, 100 μg/mL of streptomycin and 300 μg/mL hygromycin B (Gibco, Carlsbad, Calif.).

Protein Extraction and Immunoprecipitation

For protein extraction from murine tracheal smooth muscle cells (mTSMCs) and human bronchial smooth muscle cells (hBSMCs), cells were treated with the indicated drugs/peptides and immediately lysed in cold lysis buffer containing 120 mmol/L NaCl, 50 mmol/L Tris-HCl (pH 8.0), complete protease inhibitors (Roche Applied Science, Indianapolis, Ind.) and phosphatase inhibitors (50 mmol/L sodium fluoride, 1 mmol/L sodium orthovanadate and 10 mmol/L sodium pyrophosphate). After 30 min of incubation on ice, lysates were centrifuged at 13000 rpm for 10 min at 4° C. and used for either Western blotting or subjected to immunoprecipitation and measurements of phosphodiesterase activity.

For immunoprecipitation assays, protein extracts were pre-incubated with 30 µL of a 1:1 mixture of protein A or G and sepharose (Amersham Biosciences, Buckinghamshire, UK) and subsequently incubated with 20 µL of a 1:1 mixture of protein A or G and sepharose and 1 mg of primary antibody for each mg of protein, for 2 hours at 4° C. Immune complexes were washed extensively with lysis buffer and used for Western blotting or subjected to measurements of phosphodiesterase activity.

FRET Imaging and Analysis

Measurements of cAMP levels were performed on human bronchial smooth muscle cells (hBSMCs) that express the FRET probe ICUE3, as described previously (2). Briefly, cells were maintained in a K$^+$-Ringer solution containing (in mmol/L) 121.6 NaCl, 5.4 KCl, 1.8 MgCl$_2$, 1.8 CaCl$_2$, 4 NaHCO$_3$, 0.8 NaH$_2$PO$_4$, 5 D-glucose, 5 sodium pyruvate, 10 HEPES, at pH 7.4. FRET recordings were carried out before and after adding 100 nmol/L of isoproterenol (Iso) and 100 nmol/L of CGP-20712A (CGP), using a SP5 Leica TCS system (Leica Microsystems Inc., Buffalo Grove, Ill., USA) with an argon laser and with a 63× immersion lens. To excite CFP and YFP, 458 and 514 nm wavelengths were used, respectively. Images were acquired every 4 seconds without any media line, at a scanning speed of 400 MHz and a resolution of 512×512 pixels. FRET efficiency was calculated using the "Method 3" provided by the Leica wizard application for FRET imaging and sensitized emission, according to which: $E_A(i)=B/A$, where $E_A(i)$ is the apparent FRET efficiency; A and B are the intensities of the CFP channel and FRET, respectively. For imaging in hBSMCs treated with peptides, cells expressing the FRET indicator ICUE3 were pre-incubated with 50 µM of the Trojan peptide derived from PI3Kγ (SEQ ID No.: 2-RQIKIWFQNRRMKWKKGKATHR-SPGQIHLVQRHPPSEESQAF) or the P1 control peptide (SEQ ID No.: 3-RQIKIWFQNRRMKWKK) for 30 minutes prior to treatment with Iso and CGP.

Phosphodiesterase Activity Assay

Phosphodiesterase activity in immunoprecipitates was measured according to the two-step method of Thompson and Appleman, as previously described (2), with minor modifications. Briefly, immunoprecipitates were assayed in a total volume of 200 µL of reaction mixture containing 40 mmol/L Tris-HCl (pH 8.0), 1 mmol/L MgCl$_2$, 1.4 mmol/L 2-mercapto-ethanol and 0.1 pCi of [$^3$H] cAMP (Amersham Bioscience, Buckinghamshire, UK) for 40 min at 33° C. To stop the reaction, samples were boiled at 95° C. for 3 min. The reaction product 5'-AMP was then hydrolyzed by incubation of the mixture with 50 µg of snake venom from Crotalus Atrox for 15 min at 37° C. (Sigma-Aldrich, St. Louis, Mo.). The resulting adenosine was separated by anion exchange chromatography with 400 µL of a suspension of Dowex resin AG1-X8 (Bio-Rad, Segrate, Milan, Italy), water and 100% ethanol in equal parts. The amount of radiolabeled adenosine in the supernatant was quantified by scintillation counting (Ultima Gold liquid scintillation from Perkin Elmer, Waltham, Mass.).

Isolation of Mouse Tracheal Smooth Muscle Cells

Murine tracheal smooth muscle cells were cultured from explants of trachea using previously described methods with modifications. The entire trachea between the larynx and bronchi was removed and placed in a sterile Petri dish containing Hanks's balanced salt solution at room temperature and a 2× concentration of antibiotic-antimycotic (Gibco, Carlsbad, Calif., product code: 15240-062). Using a dissecting microscope, the additional surrounding tissue was removed, the tracheal segment was divided longitudinally and cut into squares of 2-3 mm in size. All the segments of a single trachea were then placed with the inner face towards the bottom of a 60 mm sterile cell culture plate. After adherence of the explants to the plate, 2.5 ml of Dulbecco's Modified Eagle Medium (DMEM, Gibco, Carlsbad, Calif.), supplemented with 20% fetal bovine serum was added to cover the explants. Explants were incubated at 37° C. in a humidified atmosphere with 95% air and 5% CO$_2$. Three days after plating, the concentrations of FBS and antibiotic-antimycotic were reduced to 10% and 1×, respectively. Tracheal segments were removed when cells became locally confluent. Once the 60 mm plate became confluent, cells were detached by trypsinization and transferred to a single 60 mm plate. Tracheal smooth muscle cells were further subdivided for several passages in a 1:2 ratio. More than 90% of these cells were smooth muscle cells, as determined by immunofluorescence performed with an antibody specific for smooth muscle actin. All experiments were performed on confluent cells at passage 3.

Measurements of Calcium Transients hBSMCs were loaded with the calcium indicator Indo-1-AM (2 µM, Invitrogen, Carlsbad, Calif.) at 37° C. for 40 minutes in the presence of P1 control peptide, Trojan peptide derived from PI3Kγ or vehicle. Cells were washed with a Tyrode solution containing (in mmol/L): 5 HEPES, 154 NaCl, 4 KCl, 2 CaCl$_2$, 1 MgCl$_2$, 5.5 D-glucose, at pH 7.35 and placed on an inverted microscope. Cells were kept in Tyrode solution and treated with a KCl depolarizing solution containing (in mmol/L): 5 HEPES, 118 NaCl, 40 KCl, 2 CaCl$_2$, 1 MgCl$_2$, 5.5 D-glucose, at pH 7.35. Calcium transients were analyzed as the ratio of fluorescence signals measured at 400 nm and 490 nm following excitation of Indo-1-AM-loaded cells at 350 nm. Experiments were recorded and analyzed with Igor® Software, using the functions added by Jason Rothman (Neuromatic, www-.thinkrandom.com).

Measurements of Chloride Currents in the Ussing Chamber

To measure chloride currents in normal and ΔF508 primary human bronchial epithelial cells, cells were cultured on 1.12 cm$^2$ Snapwell inserts. Filters were mounted in Ussing chambers, and a chloride gradient was applied by incubating the cells in a basolateral high-chloride buffer containing (in mmol/L): 140 NaCl, 5 KCl, 0.36 K$_2$HPO$_4$, 0.44 KH$_2$PO$_4$, 1.3 CaCl$_2$, 0.5 MgCl$_2$, 4.2 NaHCO$_3$, 10 HEPES, and 10 glucose, at pH 7.4 and an apical low-chloride buffer containing (in mmol/L): 133.3 Na-gluconate, 5 K-gluconate, 2.5 NaCl, 0.36 K$_2$HPO$_4$, 0.44 KH$_2$PO$_4$, 5.7 CaCl$_2$, 0.5 MgCl$_2$, 4.2 NaHCO$_3$, 10 HEPES, and 10 mannitol, at pH 7.4. Buffers were aerated with a mixture of 95% O$_2$ and 5% CO$_2$ and the temperature was maintained at 37° C. during the experiment. Cultures were maintained at a voltage of 0 mV using an EVC4000 MultiChannel V/I Clamp (World Precision Instruments, Sarasota, Fla., USA). After a stabilization period of 30 minutes, drugs were added at specific times, while the current was continuously recorded.

cAMP Extraction and Quantification

Lungs and trachea were explanted from animals following euthanasia, pulverized in liquid nitrogen and used for cold extraction of cAMP with 6% trichloroacetic acid. Samples were sonicated for 10 seconds and centrifuged at 13000 rpm at 4° C. for 15 minutes. Supernatants were washed four times with five volumes of diethyl ether saturated with water and lyophilized. cAMP content was detected with an Amersham cAMP BioTrak Enzymeimmunoassay System (GE Healthcare Life Sciences, Pittsburgh, USA, product code: RPN225), according to the manufacturer's protocol.

Analysis of the Transduction Efficiency of the Trojan Peptide Derived from PI3Kγ In Vivo hBSMCs were incubated with the Trojan peptide derived from PI3Kγ (SEQ ID No.: 2) conjugated to fluorescein (50 µM) or vehicle for 30 minutes, fixed with 4% paraformaldehyde (PFA) for 10 minutes and permeabilized with phosphate-buffered saline (PBS)+0.5% Triton (Sigma-Aldrich, St. Louis, Mo.) for 5 minutes at room temperature. Cells were then incubated with PBS containing 3% bovine serum albumin (BSA, Sigma-Aldrich, St. Louis, Mo.) and phalloidin-Alexa 488 (1:1000, Thermo Fisher Scientific, Waltham, Mass., USA) for 30 minutes and mounted on microscope slides with ProLong@ Antifade Reagent (Thermo Fisher Scientific, Waltham, Mass., USA). Red (actin) and FITC (peptide) fluorescence images were acquired with a Zeiss Observer-Z1, equipped with an Apotome module (Carl Zeiss, Oberkochen, Germany).

Wild-type BALB/C mice were injected by the intra-tracheal route with 1.5 µg of the Trojan peptide derived from PI3Kγ conjugated to fluorescein or vehicle, in a final volume of 70 µL of PBS. After 30 minutes, animals were anesthetized, the trachea and lungs were insufflated with PBS, extracted and frozen in OCT. Cryosections of 10 microns were obtained with a Leica CM1850 cryostat (Leica Microsystems GmbH, Wetzlar, Germany) and fluorescence was acquired with a Zeiss Observer-Z1, equipped with an Apotome module (Carl Zeiss, Oberkochen, Germany).

Immunization with Ovalbumin

Ovalbumin (100 µg) (OVA, Sigma-Aldrich, St. Louis, Mo.), complexed with aluminum potassium sulfate (1 mg, alum) was administered intraperitoneally (i.p.) on days 1 and 14, and intra-nasally (i.n.) (50 µg OVA in 50 µl PBS) on days 14, 25, 26, and 27. Control mice received i.p. injections of alum and i.n. injections of PBS only. Airway hyperreactivity induced by inhaled methacholine was measured at 24 hours after the final dose of OVA (Day 28).

Measurement of Airway Reactivity

Method 1. Mice sensitized to ovalbumin were anesthetized (sodium pentobarbital, 70-90 mg/kg, i.p.), tracheotomized, and connected to a FlexiVent ventilator for small animals (SCIREQ, Montreal, Quebec, Canada). To induce airway constriction, mice were exposed to increasing concentrations of aerosolized methacholine ($10^{-9}$ to $10^{-4}$ M, final concentration).

Method 2: Mice sensitized to ovalbumin were treated, by intra-tracheal instillation, with 70 µL of phosphate-buffered saline solution (PBS) containing vehicle or 150 µg of the Trojan peptide derived from PI3Kγ or equimolar amounts of P1 control peptide. Airway hyperresponsiveness was assessed at 30 minutes after the treatment according to a previously published protocol (6). Briefly, mice were anesthetized (sodium pentobarbital, 70-90 mg/kg, i.p.), tracheotomized, and ventilated with a positive end-inspiratory pressure of 10 cm $H_2O$, positive end-expiratory pressure (PEEP) of 3 cm $H_2O$, respiratory rate of 90 breaths/min in ambient air. The airway opening pressure (Pao), proximal to the endotracheal tube, and the pressure inside the chamber were measured with pressure transducers (Special Instruments, Digima Clic; Nordlingen, Germany). Gas flow was measured with a pneumotachograph (Special Instruments, Digima Clic; Nordlingen, Germany). Tidal volume was calculated as the integral of the flow signal. Variables of mechanical ventilation were recorded using the ICU-Lab software (KleisTEK Advanced Electronic Systems, Bari, Italy). Airway hyperreactivity was assessed as a change in tidal volume after treatment with 500 mg/kg of methacholine administered intravenously.

Analysis of Airway Inflammation in Asthmatic Mice

Wild-type BALB/C mice were treated, by intra-tracheal instillation, with 25 µg of the Trojan peptide derived from PI3Kγ or equimolar amounts of P1 control peptide, in a final volume of 70 µL of phosphate-buffered saline (PBS), before each intranasal administration of ovalbumin (days 14, 25, 26, and 27 of the protocol of immunization with ovalbumin). At 24 hours after the final injection (day 28), mice were anesthetized (sodium pentobarbital, 70-90 mg/kg, i.p.) and the tracheas incised and cannulated. The airways were washed with 2.5 ml of phosphate-buffered saline solution (PBS). The total number of cells in the bronchoalveolar lavage (BAL) was determined with a Neubauer hemocytometer. A volume of 50 µL of BAL was centrifuged onto cytospin glass slides at 400 rpm at room temperature for 5 minutes and stained with a Diff-Quick system (LabAids, Ronkonkoma, USA). A total of 100 cells per slide were counted and classified as neutrophils, macrophages, lymphocytes and eosinophils on the basis of morphological criteria. Erythrocytes and epithelial cells were ignored and the results were expressed as cells/ml.

To assess the peribronchial inflammation, the lungs of a group of animals that had not been subjected to bronchoalveolar lavage were explanted, fixed in a solution of 4% paraformaldehyde (PFA) for 24 hours at 4° C. and embedded in paraffin. Slices that were 5 µm-thick, deparaffinized, stained with a hematoxylin-eosin solution (Bio-Optica, Milano, Italy), dehydrated and mounted with glass coverslips. The extent of peribronchial inflammation was classified as follows: 0—normal; 1—few inflammatory cells; 3—a thick ring of inflammatory cells.

To evaluate the presence of goblet cells, lung slices were stained with periodic acid-Schiff's reagent (PAS) (Bio-Optica, Milano, Italy) and the percentage of PAS-positive cells was calculated by counting the number of PAS-positive epithelial cells and total epithelial cells.

Antibodies, Reagents and Plasmids

PDE4B and PDE4D were immunoprecipitated as described previously (2), using polyclonal rabbit antibodies freely available from Dr. Marco Conti at the University of California San Francisco, San Francisco, Calif., USA. Commercial antibodies specific for PDE4B and PDE4D can be purchased from Abcam (Abcam, Cambridge, Mass., USA): anti-PDE4B product code: ab14611; anti-PDE4D product code: ab14614. Rabbit polyclonal antibodies against $Ca_v1.2$ and phospho-$Ca_v1.2$ are freely available from Dr. William A. Catterall at the University of Washington, Seattle, Wash., USA.

The antibody that recognizes substrates phosphorylated by PKA (P-PKA substrate) was purchased from Cell Signaling Technology (Danvers, Mass., USA; product code: #9621) and the antibody against CFTR clone M3A7 from Millipore (Billerica, Mass., USA; product code: 05-583).

ICUE3-pcDNA3 was described previously (2).

Isoproterenol, CGP-20712A, carbachol, Rolipram, amiloride and forskolin were all purchased from Sigma (Sigma-Aldrich, St. Louis, Mo.). The CFTR corrector VX-809, the CFTR potentiator VX-770 and the CFTR inhibitor 172 were purchased from Selleckchem (Houston, Tex., USA).

The P1 control peptide (SEQ ID No.: 3-RQIKIWFQNRRMKWKK) and the Trojan peptide derived from PI3Kγ (SEQ ID No.: 2-RQIKIWFQNRRMKWKKGKATHR-SPGQIHLVQRHPPSEESQAF) were synthesized by GenScript (GenScript, Piscataway, N.J., USA) and Chinapeptides (Chinapeptides Co. Ltd., Shanghai, China).

Statistical Analysis

Prism software (GraphPad Software Inc., La Jolla, Calif., USA) was used for statistical analysis. P values were calculated using the Student's t test, one-way or two-way ANOVA followed by Bonferroni test, as appropriate. In all the figures, graphs represent the mean value±standard error of at least 3 independent experiments.

Results

A Trojan Peptide Derived from PI3Kγ Enhances 02-AR/cAMP Signaling in Bronchial Smooth Muscle Cells Strategies to increase cAMP levels downstream of $\beta_2$-ARs in bronchial smooth muscle are of great interest for treating respiratory diseases. To explore the therapeutic potential of inhibiting PI3Kγ-dependent $\beta_2$-AR-cAMP signaling, a peptide inhibitor of the kinase-independent activity of PI3Kγ, the sequence of which is shown in SEQ ID No.: 2, was designed. A previous study indicates that a peptide comprising the 126-150 residues of human PI3Kγ (SEQ ID No.: 1) inhibits PKA anchoring and decreases the activity of PI3Kγ-bound phosphodiesterase 3B in vitro (1). To inhibit the PKA anchoring activity of PI3Kγ in vivo, an inhibitory fusion peptide permeable to cell membranes was obtained by binding the 126-150 domain of human PI3Kγ (SEQ ID No.: 1) with the Trojan peptide of Antennapedia Penetratin 1 (SEQ ID No.: 3—FIG. 1A). A version of the PI3Kγ inhibitory Trojan peptide labeled with fluorescein (FITC) accumulated in the cytoplasm of human bronchial smooth muscle cells (hBSMCs) at 30 minutes after incubation, showing that the inhibitor is efficiently transduced in vivo in isolated cells (FIG. 1B). In addition, the PI3Kγ inhibitory peptide significantly reduced the catalytic activity of PDE4B and PDE4D in tracheal smooth muscle cells of wild-type mice (PI3Kγ$^{+/+}$), but not of animals devoid of the enzyme (PI3K$^{-/-}$) (FIG. 1C), demonstrating the ability of the peptide to selectively interfere with PI3Kγ-dependent anchoring of PKA. In accordance with these data, pre-treatment of hBSMCs with the PI3Kγ inhibitory Trojan peptide increased cAMP accumulation by 35% following stimulation of $\beta_2$-ARs, while cAMP levels were unchanged in cells treated with P1 control peptide (FIGS. 1D and E).

Since cAMP is known to induce a decrease of intracellular levels of $Ca^{2+}$ and, as a consequence, to promote smooth muscle relaxation, the ability of the PI3Kγ inhibitory Trojan peptide to modify $Ca^{2+}$ concentrations in hBSMCs was analyzed. The maximum peak of $Ca^{2+}$ transients induced by the muscarinic agonist carbachol was significantly lower in hBSMCs pre-treated with the PI3Kγ inhibitor compared to cells exposed to vehicle or to P1 control peptide (FIG. 2A-B). The primary mechanism by which cyclic nucleotides limit intracellular $Ca^{2+}$ in smooth muscle cells is the inhibition of voltage-dependent $Ca^{2+}$ channels (VOCCs).

Moreover, it has been previously demonstrated that PI3Kγ is a key regulator of cAMP in the vicinity of these $Ca^{2+}$ channels (2). To verify whether inhibiting the anchoring activity of PI3Kγ impairs the influx of $Ca^{2+}$ through VOCCs, hBSMCs were exposed to a solution containing KCl, able to depolarize the membrane and, therefore, to activate VOCCs. The influx of $Ca^{2+}$ induced by KCl was completely abolished by the PI3Kγ inhibitory Trojan peptide, while it was unchanged in hBSMCs treated with P1 control peptide or vehicle (FIG. 2A-B). To further support these results, the cAMP-mediated phosphorylation of the pore-forming subunit of the $Ca^{2+}$ channel, $Ca_v1.2$, was found to be significantly higher in hBSMCs treated with the inhibitor of PI3Kγ compared to control cells treated with vehicle or with the P1 peptide (FIG. 2C).

Overall, these data indicate that a Trojan peptide that inhibits the PKA anchoring function of PI3Kγ constitutes a novel method for inhibiting selected PDEs and enhancing cAMP signaling downstream of $\beta_2$-ARs, in smooth muscle cells.

A Trojan Peptide Derived from PI3Kγ Limits Airway Hyperresponsiveness in Healthy and Asthmatic Mice To determine the transduction efficiency of the PI3Kγ inhibitory peptide in vivo in the airways, a fluorescein (FITC)-labelled form of the peptide was instilled by the intra-tracheal route in BALB/C wild-type mice. FITC fluorescence was detected in the trachea and lungs, but not in the brain or in the myocardium, at 30 minutes after administration (FIG. 3A); this demonstrates that the peptide is efficiently distributed in the respiratory tract of the animals. In addition, cAMP levels were 30% higher in the trachea and in the lungs of mice injected with the PI3Kγ inhibitory Trojan peptide compared to control animals treated with phosphate-buffered saline solution (PBS) or P1 control peptide (FIG. 3B). In agreement with an enhanced cAMP accumulation in the respiratory tract, airway hyperreactivity induced by the muscarinic agonist methacholine was significantly attenuated by the PI3Kγ inhibitory peptide, but not by the P1 control peptide, in healthy mice (FIG. 5C). To verify if the intra-tracheal administration of the Trojan peptide derived from PI3Kγ suppresses the airway hyperresponsiveness associated with allergic asthma, a pre-clinical model of ovalbumin (OVA)-induced asthma was generated. The reduction of the tidal volume induced by methacholine was significantly attenuated in animals treated with the PI3Kγ inhibitory peptide compared to control mice, which received PBS or the P1 peptide (FIG. 3D).

Taken together, these data demonstrate the ability of the Trojan peptide derived from PI3Kγ to increase cAMP levels in vivo in the airways and to function as a bronchodilator.

A Trojan Peptide Derived from PI3Kγ Increases cAMP Levels and Enhances the Conductance of CFTR in Bronchial Epithelial Cells Expressing Wild-Type or a ΔF508 Mutant CFTR Subsequently, the ability of the PI3Kγ inhibitory Trojan peptide to increase cAMP levels not only in smooth muscle cells, but also in epithelial cells of the airways, was examined. For this purpose, we analyzed cAMP-mediated phosphorylation of the cystic fibrosis transmembrane conductance regulator (CFTR), the main chloride (Cl$^-$) channel in the epithelium of the respiratory tract, the activation of which is cAMP-dependent. CFTR phosphorylation was significantly higher in normal human bronchial epithelial cells (Nuli-1) treated with the Trojan peptide derived from PI3Kγ, compared to control cells exposed to vehicle or to P1 control peptide (FIG. 4A). In particular, inhibition of the anchoring function of PI3Kγ further enhanced cAMP-dependent CFTR phosphorylation induced by a known inhibitor of PDE4 (FIG. 4B), suggesting that the PI3Kγ inhibitory peptide not only inhibits PDE4, but also other PDE isoforms known to be associated with PI3Kγ, such as PDE3 (2).

To examine whether increased CFTR phosphorylation correlates with higher Cl⁻ conductance, measurements of Cl⁻ currents were performed in Ussing chambers in NuLi-1 cells expressing wild-type CFTR. CFTR-dependent currents increased significantly following the application of the Trojan peptide derived from PI3Kγ, while the P1 control peptide did not change the conductance (FIG. 4C). These data thus reveal a novel role for the PI3Kγ inhibitory peptide as a CFTR potentiator.

Molecules with CFTR potentiator activity are required to stimulate the opening of the defective CFTR in the treatment of cystic fibrosis (CF). To determine if the Trojan peptide derived from PI3Kγ is able to correct the defective Cl⁻ conductance of the mutant CFTR, CFTR-dependent currents were measured in bronchial epithelial cells expressing the mutant CFTR ΔF508-CFTR (CuFi-1). PI3Kγ inhibition synergistically increased the activity of the known CFTR potentiator, VX-770, resulting in an increase of the CFTR currents by about 5-fold more than the basal activity (FIGS. 4A and B). By contrast, the P1 control peptide did not change the CFTR activity of in the presence of VX-770 (FIGS. 4A and B).

Overall, these data reveal a novel function for the PI3Kγ inhibitory peptide as a CFTR potentiator, which promotes cAMP-dependent opening of the wild-type channel and the mutant CFTR(ΔF508-CFTR).

A PI3Kγ-Derived Trojan Peptide Limits Lung Inflammation in Asthmatic Mice

It is well known that an increase of cAMP in leukocytes promotes an anti-inflammatory response. Therefore, the ability of the PI3Kγ-derived Trojan peptide to increase cAMP concentrations in this cell type and, therefore, to limit the inflammation associated with chronic respiratory diseases, was evaluated. Mice pre-treated with the P1 control peptide before each intranasal injection of ovalbumin showed an increase in peribronchial inflammation (FIGS. 7A and B), and in the number of goblet cells, containing mucus and positive to the periodic acid-Schiff's reagent (PAS) staining (FIGS. 7A and C), compared to control animals not sensitized to ovalbumin (naïve). The Trojan peptide derived from PI3Kγ significantly reduced both the peribronchial inflammatory infiltrate (FIGS. 7A and B) and the number of goblet cells (FIGS. 7A and C). In agreement with these results, the number of neutrophils present in the bronchoalveolar lavage was significantly lower in the animals treated with the PI3Kγ inhibitory Trojan peptide compared to controls that received the P1 peptide (FIG. 7D). By contrast, other leukocyte populations such as macrophages, lymphocytes and eosinophils were unchanged (FIG. 7E-F-G).

Overall, this experimental evidence demonstrates the ability of the Trojan peptide derived from PI3Kγ to selectively inhibit the neutrophilia associated with chronic respiratory diseases, and therefore to function as an anti-inflammatory drug.

REFERENCES

1. A. Perino et al., *Mol Cell* 42, 84 (Apr. 8, 2011).
2. A. Ghigo et al., *Circulation* 126, 2073 (Oct. 23, 2012).
3. M. Della Peruta, C. Giagulli, C. Laudanna, A. Scarpa, C. Sorio, *Mol Cancer* 9, 61 (2010).
4. E. Hirsch et al., *Science* 287, 1049 (Feb. 11, 2000).
5. E. Patrucco et al., *Cell* 118, 375 (Aug. 6, 2004).
6. V. Fanelli et al., *Intensive Care Med* 36, 1935 (November 2010).

The invention claimed is:

1. A product comprising
   a) at least one fusion peptide, wherein the fusion peptide comprises:
      i) the amino acid sequence as defined in SEQ ID No.: 1 or a related homolog having at least 90% identity with SEQ ID No.: 1 and having the ability of the sequence SEQ ID No.: 1 to inhibit the kinase-independent function of PI3Kγ, and
      ii) a peptide having the ability to penetrate a cell; and
   b) at least one potentiator of the cystic fibrosis transmembrane conductance regulator (CFTR) and/or at least one corrector of the cystic fibrosis transmembrane conductance regulator (CFTR),
   wherein the fusion peptide and the potentiator and/or corrector are formulated for sequential, simultaneous or separate administration.

2. The product according to claim 1, wherein the potentiator of the cystic fibrosis transmembrane conductance regulator (CFTR) is selected from VX-770 (N-(2,4-Di-tert-butyl-5-hydroxyphenyl)-1, 4-dihydro-4-ossoquinolin-3-carboxamide) and VX-532 (4-Methyl-2-(5-phenyl-1H-pyrazol-3-yl)-phenol).

3. The product according to claim 1, wherein the corrector of the cystic fibrosis transmembrane conductance regulator (CFTR) is selected from VX-809 (3-(6-(1-(2,2-difluorobenzo[d][1,3]dioxol-5-yl)cyclopropanecarboxamido)-3-methylpyridin-2-yl)benzoic acid) and VX-661 ((R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide).

4. The product according to claim 1, wherein the potentiator of the cystic fibrosis transmembrane conductance regulator (CFTR) is selected from VX-770 (N-(2,4-Di-tert-butyl-5-hydroxyphenyl)-1, 4-dihydro-4-ossoquinolin-3-carboxamide) and VX-532 (4-Methyl-2-(5-phenyl-1H-pyrazol-3-yl)-phenol), and wherein the corrector of the cystic fibrosis transmembrane conductance regulator (CFTR) is selected from VX-809 (3-(6-(1-(2,2-difluorobenzo[d][1,3]dioxol-5-yl)cyclopropanecarboxamido)-3-methylpyridin-2-yl)benzoic acid) and VX-661 (R)-1-(2,2-difluorobenzo[d][1,3]dioxol-5-yl)-N-(1-(2,3-dihydroxypropyl)-6-fluoro-2-(1-hydroxy-2-methylpropan-2-yl)-1H-indol-5-yl)cyclopropanecarboxamide).

5. The product according to claim 1, wherein the fusion peptide and the potentiator and/or corrector are formulated for separate administration.

6. The product according to claim 5, wherein the fusion peptide is formulated for administration by inhalation.

7. The product according to claim 1, wherein the fusion peptide comprises the amino acid sequence as defined in SEQ ID No.: 1.

8. The product according to claim 1, wherein the peptide having the ability to penetrate a cell has the amino acid sequence as defined in SEQ ID No.: 3.

9. The product according to claim 1, wherein the fusion peptide has the amino acid sequence set forth in SEQ ID No.: 2.

10. The product according to claim 1, wherein the peptide having the ability to penetrate a cell is selected from the sequences specified in SEQ ID No.: 3 to 12.

11. The product according to claim 10, wherein the fusion peptide comprises the amino acid sequence as defined in SEQ ID No.: 1.

* * * * *